(12) United States Patent
Ulmer

(10) Patent No.: US 7,593,109 B2
(45) Date of Patent: *Sep. 22, 2009

(54) APPARATUS AND METHODS FOR ANALYZING SAMPLES

(75) Inventor: Kevin Ulmer, Cohasset, MA (US)

(73) Assignee: Helicos BioSciences Corporation, Cambridge, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 11/865,653

(22) Filed: Oct. 1, 2007

(65) Prior Publication Data

US 2008/0239304 A1    Oct. 2, 2008

Related U.S. Application Data

(63) Continuation of application No. 10/990,242, filed on Nov. 16, 2004, now Pat. No. 7,276,720.

(60) Provisional application No. 60/589,170, filed on Jul. 19, 2004.

(51) Int. Cl.
*G01N 21/00* (2006.01)
*G01N 21/85* (2006.01)

(52) U.S. Cl. ............... 356/436; 250/576; 250/558.1

(58) Field of Classification Search ............... None
See application file for complete search history.

(56) References Cited

U.S. PATENT DOCUMENTS

| | | | |
|---|---|---|---|
| 3,957,470 A | 5/1976 | Dawes | |
| 4,060,182 A | 11/1977 | Kikuchi | |
| 4,108,602 A | 8/1978 | Hanson et al. | |
| 4,192,071 A | 3/1980 | Erickson | |
| 4,365,409 A | 12/1982 | Riley et al. | |
| 4,596,648 A | 6/1986 | Sweeney | |
| 4,606,296 A | 8/1986 | Gailliard et al. | |
| 4,689,688 A | 8/1987 | Michon | |
| 4,772,256 A | 9/1988 | Lane et al. | |
| 4,778,451 A | 10/1988 | Kamen | |
| 4,879,431 A | 11/1989 | Bertoncini | |
| 4,958,295 A | 9/1990 | Davidson et al. | |
| 4,978,566 A | 12/1990 | Scheurer et al. | |
| 5,034,194 A | 7/1991 | Miller et al. | |

(Continued)

FOREIGN PATENT DOCUMENTS

DE    102 58 945 A1    7/2004

(Continued)

OTHER PUBLICATIONS

Sako, Y. et al., "Single-Molecule Imaging of EGFR Signalling on the Surface of Living Cells", Nature Cell Biology, 2:168-172 (2000).

(Continued)

*Primary Examiner*—Gregory J Toatley, Jr.
*Assistant Examiner*—Amanda H Merlino
(74) *Attorney, Agent, or Firm*—Cooley Godward Kronish LLP

(57) ABSTRACT

The present invention relates to apparatus, systems, and methods for analyzing biological samples. The apparatus, systems, and methods can involve using a vacuum source to pull microfluidic volumes through analytical equipment, such as flow cells and the like. Additionally, the invention involves using optical equipment in conjunction with the analytical equipment to analyze samples and control the operation thereof.

13 Claims, 15 Drawing Sheets

U.S. PATENT DOCUMENTS

| | | | |
|---|---|---|---|
| 5,304,303 | A | 4/1994 | Kozak, III |
| 5,329,347 | A | 7/1994 | Wallace et al. |
| 5,345,079 | A | 9/1994 | French et al. |
| 5,370,221 | A | 12/1994 | Magnusson et al. |
| 5,395,588 | A | 3/1995 | North, Jr. et al. |
| 5,643,193 | A | 7/1997 | Papillon et al. |
| 5,679,310 | A | 10/1997 | Manns |
| 5,711,865 | A | 1/1998 | Caesar |
| 5,748,315 | A | 5/1998 | Kawai et al. |
| 5,875,360 | A | 2/1999 | Osawa |
| 5,971,948 | A | 10/1999 | Pages et al. |
| 6,016,193 | A | 1/2000 | Freeman et al. |
| 6,098,843 | A | 8/2000 | Soberanis et al. |
| 6,184,535 | B1 | 2/2001 | Kashima et al. |
| 6,225,955 | B1 | 5/2001 | Chang et al. |
| 6,226,129 | B1 | 5/2001 | Fukunage |
| 6,240,055 | B1 | 5/2001 | Takamine et al. |
| 6,269,975 | B2 | 8/2001 | Soberanis et al. |
| 6,315,952 | B1 | 11/2001 | Sklar |
| 6,331,431 | B1 | 12/2001 | Glaser et al. |
| 6,340,098 | B2 | 1/2002 | Soberanis et al. |
| 6,375,817 | B1 | 4/2002 | Taylor et al. |
| 6,400,487 | B1 | 6/2002 | Harris et al. |
| 6,433,325 | B1 | 8/2002 | Trigg |
| 6,499,863 | B2 | 12/2002 | Dewald |
| 6,528,309 | B2 | 3/2003 | Levine |
| 6,547,406 | B1 | 4/2003 | Greenaway et al. |
| 6,582,903 | B1 | 6/2003 | Rigler et al. |
| 6,595,006 | B2 | 7/2003 | Thiesen et al. |
| 6,605,475 | B1 | 8/2003 | Taylor et al. |
| 6,649,893 | B2 | 11/2003 | Fujimoto et al. |
| 6,666,845 | B2 | 12/2003 | Hooper et al. |
| 6,675,987 | B2 | 1/2004 | Soberunie et al. |
| 6,692,702 | B1 | 2/2004 | Burshteyn et al. |
| 6,716,002 | B2 | 4/2004 | Higashino |
| 6,720,593 | B2 | 4/2004 | Tsunai |
| 6,739,478 | B2 | 5/2004 | Bach et al. |
| 6,749,575 | B2 | 6/2004 | Matriano et al. |
| 6,750,435 | B2 | 6/2004 | Ford |
| 6,752,601 | B2 | 6/2004 | Takeuchi et al. |
| 6,756,616 | B2 | 6/2004 | Rhodes |
| 6,756,618 | B2 | 6/2004 | Hong |
| 6,767,312 | B2 | 7/2004 | Shim |
| 6,775,567 | B2 | 8/2004 | Cable et al. |
| 6,777,661 | B2 | 8/2004 | Summa et al. |
| 7,276,720 | B2 * | 10/2007 | Ulmer .................. 250/576 |
| 2003/0142398 | A1 | 7/2003 | Leblans |
| 2003/0152490 | A1 | 8/2003 | Trulson et al. |
| 2003/0227615 | A1 | 12/2003 | Montgomery et al. |
| 2004/0257576 | A1 | 12/2004 | Kirsch et al. |
| 2006/0024678 | A1 | 2/2006 | Buzby |
| 2007/0048744 | A1 | 3/2007 | Lapidus |
| 2007/0146717 | A1 | 6/2007 | Prins et al. |

FOREIGN PATENT DOCUMENTS

| | | |
|---|---|---|
| DE | 10258945 | 7/2004 |
| GB | 2181538 A | 4/1987 |
| JP | 10-307252 | 11/1998 |
| WO | WO01/67154 | 9/2001 |
| WO | WO02/072892 | 9/2002 |
| WO | WO03/023483 A1 | 3/2003 |
| WO | WO 03/023483 A2 | 3/2003 |

OTHER PUBLICATIONS

Thompson, N. et al., "Measuring Surface Dynamics of Biomolecules by Total Internal Reflection Fluorescence with Photobleaching Recovery or Correlation Spectroscopy", Biophys. J., vol. 33, pp. 435-454 (Mar. 1981).

Thompson, N. et al., "Immunoglobulin Surface-Binding Kinetics Studied by Total Internal Reflection with Fluorescence Correlation Spectroscopy", Biophys. J, vol. 43, pp. 103-114 (Jul. 1983).

Tokunaga, M. et al., "Single Molecule Imaging of Fluorophores and Enzymatic Reactions Achieved by Objective-Type Total Internal Reflection Fluorescence Microscopy", Biochem. And Biophys. Res. Comm., vol. 235, PD. 47-53 (1997).

Unger, M. et al., "Single-Molecule Fluorescence Observed with Mercury Lamp Illumination", BioTechniques, vol. 27, PD. 1008-1014 (Nov. 1999).

Vale, R. et al., "Direct observation of single kinesin molecules moving along microtubules", Nature, vol. 380, pp. 451-453, (Apr. 1996).

Watkins, R. et al. "A Total Internal-Reflection Technique for the Examination of Protein Adsorption", J. Biomed Mater. Res., 11:915-938 (1977).

Wedekind, P. et al., "Scanning microphotolysis: a new photobleaching technique based on fast intensity modulation of a scanned laser beam and confocal imaging", J. Microscopy, vol. 176, Pt. 1, pp. 23-33 (Oct. 1994).

Weiss, S., "Fluorescence Spectroscopy of Single Biomolecules", Science, vol. 283, pp. 1676-1683 (Mar. 1999).

Winter et al., "Direct gene expression analysis," Curr. Pharm. Biotech., 5, 2004, 191-197.

Pending claims (as of Nov. 7, 2008) from related U.S. Appl. No. 10/990,167 (3 pages); unpublished.

International Search Report and Written Opinion from corresponding PCT application No. PCT/US2005/024099 (12 ages), dated Oct. 25, 2005.

Bioptech, The Bioptechs Focht Chamber System 2 (FCS2) was Designed to these Specification Guidelines,: 5 pages, (Jul. 12, 2004).

Braslavsky et al., "Sequence information can be obtained from single DNA molecules," *PNAS*, vol. 100, No. 7, pp. 3960-3964, (Apr. 1, 2003).

Hansen et al., "A robust and scalable microfluidic metering method that allows protein crystal growth by free interface diffusion," *PNAS*, vol. 99, No. 26, pp. 16531-16536, (Dec. 24, 2002).

Liu et al., "A nanoliter rotary device for polymerase chain reactions," *Electrophoresis*, vol. 23, pp. 1531-1536, (2002).

Rikukawa, "Multi-mode Imaging Inverted Microscope TE200," *Nikon*, 4 pages, (2003).

Thorsen et al., "Microfluidic Large-Scale Integration," *Science*, vol. 298, pp. 580-584, (Oct. 18, 2002).

Claims as of Dec. 30, 2008 from co-pending U.S. Appl. No. 10/990,167, 3 pgs.

Claims as of Dec. 30, 2008 from abandon U.S. Appl. No. 11/234,420, 3 pgs.

Claims as of Dec. 30, 2008 from U.S. Appl. No. 11/849,088, 3 pgs.

Claims as of Dec. 30, 2008 from U.S. Appl. No. 11/928,715, 3 pgs.

Claims as of Dec. 30, 2008 from U.S. Appl. No. 11/928,727, 3 pgs.

PCT International Search Report, International Application No. PCT/US2005/041264, Mar. 16, 2006.

Ambrose, W. et al., "Single Molecule Detection With Total Internal Reflection Excitation: Comparing Signal-to Background and Total Signals in Different Geometries", Cytometry, vol. 36, pp. 224-231 (1999).

Arndt-Jovin, D. et al., "Immunofluorescence Localization of Z-DNA in Chromosomes: Quantitation by Scanning Microphotometry and Computer-assisted Image Analysis", 1. Cell Biol., JI, vol. 101, pp. 1422-1433, (Oct. 1985).

Axelrod, D., "Cell-Substrate Contacts Illuminated by Total Internal Reflection Fluorescence", I. Cell Biol., JI, vol. 89, pp. 141-145, (Apr. 1981).

Axelrod, D. et al., "Total internal reflection fluorescent microscopy", J Microscopy, vol. 129, pp. 19-28, (1983).

Axelrod, D. et al., "Total internal reflection fluorescent microscopy", Traffic 2:764-774 (2001).

Basche, T. et al., "Single Molecule Optical Detection, Imaging and Spectroscopy", Chs. 2 and 3, Weinheim:VCM, Germany (1997).

Braslavsky, I. et al., "Objective-type dark-field illumination for scattering from microbeads", Applied Optics, vol. 40, No. 31, pp. 5650-5657, (Nov. 2001).

Burghardt, T. et al., "Total Internal Reflection Fluorescence Study of Energy Transfer in Surface-Adsorbed and Dissolved Bovine Serum Albumin", Biochemistry, vol. 22, pp. 979-985 (1983).

Crocker, J.C. and D.G. Grier, "Methods of digital video microscopy for colloidal studies." Journal of Colloid and Interface Science, 1996. 179(1): p. 298-310.

Dickson et al., "Simultaneous Imaging of Individual Molecules aligned both parallel and prependicular to the optic axis" vol. 81, No. 24, 1998.

Driscoll et al. "Atomic-Scale Imaging of DNA Using Scanning Tunneling Microscopy", Nature, 346(6281):294-296 (1990).

Evangelista, R.A., et al. "Characterization of fluorescent nucleoside triphosphates by capillary electrophoresis with laser-induced fluorescence detection: action of alkaline phosphatase and DNA polymerase." Anal Biochem, 1996.235 (1): p. 89-97.

Ferguson et al., "A fiber-optic DNA biosensor microarray for the analysis of gene expression," Nature Biotechnology, vol. 14, pp. 1681-1684 (1996).

Funatsu, T. et al., "Imaging of single fluorescent molecules and individual ATP turnovers by single myosin molecules in aqueous solution", Nature, vol. 374, pp. 555-559 (Apr. 1995).

Goodwin, P.M. et al., "Application of Singlr Molecule Detection to DNA Sequencing" Nucleosides & Nucleotides, 16 (5-6):543-550 (1997).

Gueroui, Z., et al., "Observation by fluorescence microscopy of transcription on single combed DNA." Proceedings of the National Academy of Sciences of the United States of America, 2002. 99(9): p. 6005-6010.

Guilbault, G., "Practical Fluorescence—Theory, Methods and Techniques," Chapters 1 and 3, and pp. 521-524, Marcel Dekker, Inc., New York (1973).

Ha, "Single molecule spectroscopy with automated positioning," Appl. Phys. Lett. 70, No. 6, Feb. 10, 1997, 782-784.

Ha et al., "Single-Molecule Fluorescence Spectroscopy of Enzyme Conformational Dynamics and Cleavage Mechanism", Proceedings of the National Academy of Sciences of the United States of America, 96(3):893-898 (1999).

Ha, T., "Single-molecue fluorescence resonance energy transfer." Methods, 2001. 25(1): p. 78-86.

Ha et al., "Single-Molecule Fluorescence Methods for the Study of Nucleic Acids", Current Opinion in Strct Bio, 11:287-292 (2001).

Houseal, T. et al., "Real-time imaging of single DNA molecules with fluorescence microscopy", Biophys. 1., vol. 56, pp. 507-516 (Sep. 1989).

Iskikawa, M. et al., "Single-Molecule Detection by Laser-Induced Fluorescence Technique with a Position-Sensitive Photon-Counting Apparatus", 1pn. 1.Appl. Phys., vol. 33, Part 1, No. 3A, pp. 1571-1576 (1994).

Jett, J. et al., "High-Speed DNA Sequencing: An Approach Based Upon Fluorescence Detection of Single Molecules", J Biomolecular Structure & Dynamics, vol. 7, No. 2, pp. 301-309, (1989).

Johnson, R.V., "Focus Error Detection in Optical Data Storage Systems", SPIE, 200:73-78 (1979).

Kambara, H. et al., "Optimization of Parameters in a DNA Sequenator using Fluorescence Detection", Biotechnology, vol. 6, pp. 816-821 (1988).

Kartalov et al., "Single-Molecule Detection and DNA Sequencing-by-Synthesis," In Partial Fulfillment of the Requirements for the Degree of Doctor Philosophy, California Institute of technology, pp. 1-160 (2004).

Lacoste, T. et al., "Ultrahigh-resolution multicolor colocalization of single fluorescent ptobes", PNAS, 97(17):9461-6 (2000).

Lazowski, K. et al., "Highly Sensitive Detection of Hybridization of OligonucleotideS to Specific Sequences of Nucleic Acids by Application of Fluorescence Resonance Energy Transfer", Antisense and Nucleic Acid Dru Dev., vol. 10, pp. 97-103 (2000).

Lee, Y. et al., "Laser-Induced Fluorescence Detection of a Single Molecule in a Capillary", Anal. Chem., vol. 66, pp. 4142-4149 (1994).

Li, H. et al., "Ultrasensitive Coincidence Fluorescence Detection of Single DNA Molecules", Anal. Chern., 75:1664-1670 (2003).

Lin, L. et al., "Free-Space Micromachined Optical Switches for Optical Networking", IEEE J. of Selected Topics in Quantum Electronics, vol. 5, No. 1, pp. 4-9 (Jan. 1999).

Macklin, J. et al., "Imaging and Time-Resolved Spectroscopy of Single Molecules at an Interface", Science, 272 (5259):255-258 (1996).

Marriott, G. et al., "Time resolved imaging microscopy—Phosphorescence and delayed fluorescence imaging", Biophys. J., vol. 60, pp. 1374-1387 (Dec. 1991).

Mashanov, G.I. et al., "Visualizing Single Molecules Inside Living Cells Using Total Internal Reflection Fluorescence Microscopy," Methods, 29:142-152 (2003).

Meiners, J.O. and S.R. Quake, "Femonewton force spectroscopy of single extended DNA. molecules." Phys Rev Lett, 2000. 84(21): p. 5014-7.

Mertz, J. et al., "Single-molecule detection by two-photon-excited fluorescence", Optics Letters, vol. 20, No. 24, pp. 2532-2534 (Dec. 1995).

Muller et al., "Surface-micromachined microoptical elements and systems," IEEE vol. 86, No. 8, pp. 1705-1720 (1998).

Nie, S. et al., "Probing Individual Molecules with Confocal Fluorescence Microscopy", Science, vol. 266, No. 5187, pp. 1018-1021 (Nov. 1994).

Perkins, T. et al., "Relaxation of a Single DNA Molecule Observed by Optical Microscopy", Science, 264:822-826 (May 1994).

Plakhotnik, T. et al, "Single-Molecule Spectroscopy", Annu. Rev. Phys. Chem., vol. 48, pp. 181-212 (1997).

Ploem, J., Ch. 1 "Fluorescence Microscopy", Fluorescent and Luminescent Probes for BioL Activity, Mason, T. Ed., Academic Press, London, pp. 1-11 (1993).

Qin, P. et al., "Site-Specific Labeling of RNA with Fluorophores and Other Structural Probes", Methods, vol. 18, No. 1, pp. 60-70 (May 1999).

Qin et al., "Elastomeric Light Valves", Advanced Materials, 9(5):407-410 (1997).

* cited by examiner

APPARATUS AND METHODS FOR ANALYZING SAMPLES

CROSS-REFERENCE TO RELATED APPLICATION

This application is a continuation of U.S. patent application Ser. No. 10/990,242, filed on Nov. 16, 2004, which claims priority to U.S. provisional patent application Ser. No. 60/589,170, filed on Jul. 19, 2004, the disclosures of which are incorporated herein by reference in their entirety. This application also incorporates herein by reference a U.S. patent application Ser. No. 10/990,167, filed Nov. 16, 2004.

TECHNICAL FIELD

The invention relates generally to apparatus, methods, and systems for handling and analyzing microfluidic volumes and related biological materials. Additionally, the invention relates to optical equipment, such as lighting systems, for analyzing biological samples.

BACKGROUND

Generally, systems for analyzing a sample in a flow cell are pressure driven fluidic systems using pressure pumps. Pressure driven fluidics systems have several disadvantages. One disadvantage is that pressure driven systems require the sample vessel to be sealably engaged to the flow cell assembly. This makes removal of the flow cell more complicated, because removal of the flow cell can produce hazardous aerosols. Pressure systems are also known to develop system leaks due to the pressure and may require frequent replacement of lines and valves. Additionally, pressure driven systems can introduce contaminants into the sample. Another disadvantage of pushing fluid through the system is that air can become trapped in the system or air bubbles can be introduced into the sample. Introduction of air into the pump can cause cavitation resulting in shock to the system. Moreover, in pressure driven systems, it is difficult to adequately purge the lines after each sample has been tested. This can result in residual material being left in the system when the next test is performed. Also, purging the system using air pressure tends to cause bubbling or foaming in the samples, which may introduce inaccuracies to the analysis.

The prior art vacuum driven systems that have been used to analyze samples in a flow cell also have disadvantages. In these prior art systems, a vacuum pump is directly connected to the flow cell. Again, the use of a pump can cause air bubbles to be introduced into the sample and air trapped in the pump transmit shock to the system. Additionally, the continuous on and off cycle of the pump can result in uneven passage of a sample through the flow cell. Prior art vacuum systems are also generally suited for passing multi-cell samples through the flow cell. Having a pump directly connected to the flow cell can negatively impact single-cell samples, in part, because of the shock transmitted to the system.

In analyzing microfluidic volumes and related biological materials using a light source, it is desirable for the light source to hit the sample in such a way that results in total internal reflection fluorescence ("TIRF"). TIRF is an optical phenomenon that occurs when light propagating in a dense medium, such as glass, meets an interface with a less dense medium such as water. If the light meets the surface at a small angle, some of the light passes through the interface (is refracted) and some is reflected back into the dense medium. At a certain angle, known as the critical angle, all of the light is refracted. However, some of the energy of the beam still propagates a short distance into the less dense medium, generating an evanescent wave. The evanescent wave only penetrates about 100 nm into the medium. If this energy is not absorbed, it passes back into the dense medium. However, if a flourophore molecule is within the evanescent wave, it can absorb photons and be excited. The excited fluorophores can be observed using, for example, an intensified CCD camera. Accurately maintaining the critical angle to obtain TIRF in a dynamic system is difficult.

SUMMARY OF THE INVENTION

The present invention involves using a vacuum source to pull microfluidic volumes through analytical equipment, such as flow cells and the like. Generally, the invention includes a passive vacuum source and one or more valves and sensors for operating and monitoring the apparatus and methods. Additionally, the invention involves using optical equipment in conjunction with the analytical equipment to analyze samples and control the operation thereof.

In one aspect, the invention relates to a lighting system including a first light source for analyzing a sample of interest and a second light source. The first light source defines a first optical path that intersects a sample of interest and the second light source operates with the first light source for determining a position of the first optical path.

In various embodiments of the foregoing aspect, the first light source and the second light source operate simultaneously. The second light source may define a second optical path at least partially coaxial with the first optical path. In one embodiment, the second light source is directed to a position sensor for sensing an angle of reflection of the first optical path relative to the sample of interest. The position of the first optical path can be adjusted to vary the angle of reflection in response to a signal from the position sensor. The position of the first optical path can be adjusted to obtain substantially total internal reflection of the first light source relative to the sample of interest.

Additionally, the first light source can have a wavelength from about 390 nm to about 780 nm. In one embodiment, the second light source is infrared light. The first light source and/or the second light source can be a laser, a light emitting diode, or a lamp. In one embodiment, the system includes an imaging device for imaging the sample of interest. Further, the system can include a third light source for analyzing the sample of interest. The third light source can define a third optical path at least partially coaxial with the first optical path. The first light source and the third light source can be operated simultaneously. The second light source may be used to continuously monitor the position of the first optical path. In one application, the light system can be adapted for use in a single molecule sequencing system.

In another aspect, the invention relates to a method of substantially maintaining total internal reflection for a sample of interest. The method includes the steps of providing a first beam of light for intersecting with the sample of interest, providing a second beam of light for determining a position of the first beam of light, directing the second beam of light onto a position sensor, and adjusting the position of the first beam of light in response to a signal from the position sensor to vary an angle of reflection of the first beam of light with respect to the sample of interest to substantially maintain total internal reflection.

In various embodiments, the first beam of light is at least partially coaxial with the second beam of light. The first beam of light is for analyzing the sample of interest. In one embodiment, the first light source has a wavelength from about 390 nm to about 780 nm. The second light source may be infrared light. The method may also include the steps of continuously monitoring the position of the first beam of light and adjusting the angle of reflection in response thereto to substantially maintain total internal reflection.

In another aspect, the invention relates to a system for analyzing a sample. The system includes a flow cell, a passive vacuum source for pulling a volume through the flow cell, a lighting system for illuminating the sample in the flow cell, and an optical instrument for viewing the sample in the flow cell. The lighting system can be of the type described hereinabove. In one embodiment, the volume includes the sample or agents for reacting with the sample, which may be predisposed on or within the flow cell. Alternatively or additionally, the sample may adhere to or come to rest within the flow cell while the volume passes therethrough. In one embodiment, the volume and/or sample is moved through the flow cell by gravity. For example, the head pressure on the volume within an inlet to the flow cell is sufficient to move the volume through the flow cell.

In various embodiments of the foregoing aspect, the system includes a stage for receiving the flow cell, where the stage is movable in at least one direction. In one embodiment, the stage is movable in two orthogonal directions. The system may also include an image capture device for capturing an image of the sample. The image capture device can be a charge coupled device (CCD), a complementary metal oxide semiconductor device (CMOS), a charge injection device (CID), or a video camera. Additionally, the system could include a processor for collecting and processing data generated by the system, storage for storing the data, and means for displaying at least one of the data and the sample.

In another aspect, the invention relates to an apparatus for handling microfluidic volumes, such as biological samples for analysis. The apparatus can include the aforementioned passive vacuum source and flow cell. The microfluidic volume is pulled through the flow cell by the passive vacuum source. In one embodiment, the passive vacuum source includes a pump, a pump driver, such as an electric motor, and a reservoir. The pump can be connected to the reservoir and then operated to evacuate the reservoir, thereby creating a vacuum within the reservoir. In one embodiment, the vacuum pressure is from about 1" Hg to about 29" Hg. The vacuum pressure can be adjusted to vary the speed at which the microfluidic volume passes through the flow cell.

In various embodiments of the foregoing aspects, the apparatus/system can be used for single molecule detection. In one embodiment, the flow cell includes a surface for receiving a nucleotide. For example, the flow cell can include a bound nucleotide and a primer bound to the nucleotide and/or the flow cell. In particular, the flow cell can include a slide and a coverslip, where the nucleotide and/or the primer are bound to at least one of the slide and the coverslip. Additionally, the flow cell can include a channel for pulling the microfluidic volume therethrough.

In some embodiments of the foregoing aspects, the ratio of a volume of the reservoir and the microfluidic volume is between about 1,000:1 and about 2,000,000:1, or between about 50,000:1 and about 1,000,000:1, or about 200,000:1. Further, the apparatus can include valving disposed between the various components thereof. For example, the apparatus can include a valve disposed between the vacuum source, for example the reservoir, and the flow cell, wherein the valve includes an open position to connect the flow cell to the vacuum source and a closed position to isolate the flow cell from the vacuum source. The apparatus can also include a vacuum pressure indicator connected to the reservoir. Moreover, the apparatus can further include optical equipment for analyzing material within the flow cell after exposure to the microfluidic volume.

In another aspect, the invention relates to a method of detecting single molecules. The method includes the steps of depositing a sample comprising single molecules into a flow cell, the flow cell treated to identify specific molecules; applying a vacuum to the flow cell; pulling the sample through a channel defined by the flow cell; and viewing the flow cell after exposure to the sample to identify the molecules exposed to the flow cell.

In another aspect, the invention relates to a method of detecting single molecules. The method includes the steps of providing a flow cell that defines a channel that is treated to identify specific molecules, applying a vacuum to the channel to pull a sample through the channel, the sample comprising single molecules, and viewing the sample in the channel to identify the single molecules.

Various embodiments of the foregoing methods include the step of removing the vacuum from the flow cell after pulling the sample through the channel. The step of applying a vacuum can include exposing the flow cell to a passive vacuum source. In various embodiments, the sample includes a microfluidic volume including nucleotides. Additionally, the flow cell can include at least one of a slide and a coverslip treated to bind with a specific nucleotide. Further, the step of viewing the flow cell can include illuminating the flow cell with a lighting system, such as that described hereinabove. The step of viewing the flow cell can also include using an image capture device. In one embodiment, a processor is used to control the operation of the method. The processor can be used for collecting and processing data generated during the method. The method can further include the step of displaying at least one of the flow cell and the data.

In another embodiment, single nucleotide detection is accomplished by attaching template nucleic acids to a flow cell in the presence of a primer for template-dependent nucleic acid synthesis. Using a device according to the invention, a vacuum is created across the flow cell for introduction of reagents for template-dependent nucleic acid synthesis. For example, once template/primer pairs are bound to the surface of the flow cell, reagents comprising labeled or unlabeled nucleotides and a polymerase to catalyze nucleotide addition are added via an entry port. The vacuum is switched on and the reagents are exposed to the flow cell and then exit via an exit port to the reservoir. After a wash step, complementary nucleotides added to primer are detected. Preferably, reagent nucleotides are labeled with, for example, a fluorescent dye. Such dyes are observed using light microscopy. For example, cyanine dyes (cyanine-3 or cyanine-5) are useful for optical detection of incorporated nucleotides. Using optically-detectable labels, nucleic acid sequencing is conducted on a single molecule level. This means that individual template nucleic acids are positioned on the flow cell such that each is individually optically resolvable. The location of the templates is determined by, for example, the use of dye-labeled primers that hybridize to individual templates. Labeled nucleotides are flowed across the flow channel using the mechanisms described herein under conditions that allow complementary nucleotide addition to the primer. Once incorporated, the label is detected by excitation of the dye at the appropriate wavelength and by using an emission filter for detection of the emission spectrum. Emissions that occur at a location known to contain a template indicate incorporation of the labeled base at that position. By conducting these steps multiple times, a sequence is completed. Single molecule sequencing techniques are described in Braslavsky, et al., PNAS (USA), 100: 3960-3964 (2003) and copending U.S. patent application Ser. No. 09/707,737, each of which is incorporated by reference herein.

In another aspect, the invention relates to a flow cell for analyzing single molecules, such as nucleotides. The flow cell includes a slide, a coverslip, and a gasket disposed between the slide and the coverslip. The slide, the coverslip, and the gasket define a microfluidic channel for passing single molecules under vacuum. In various embodiments, the flow cell includes a nucleotide bound to the slide and/or the coverslip. In addition, the flow cell can include a primer bound to at least one of the nucleotide, the slide, and the coverslip. In one embodiment, the slide includes a plurality of nucleotides bound thereto.

In another aspect, the invention relates to a slide for use with a flow cell. The slide can include at least one nucleotide bound to a surface of the slide. The slide can be disposed within the flow cell. The slide can further include a primer bound to at least one of the slide and the nucleotide. In addition, the slide can include a plurality of nucleotides bound thereto.

In another aspect, the invention relates to a coverslip for use with a flow cell. The coverslip includes at least one nucleotide bound to a surface of the coverslip. The coverslip can be disposed within the flow cell. The coverslip can further comprise a primer bound to at least one of the coverslip and the nucleotide. In one embodiment, the coverslip includes a plurality of nucleotides bound thereto.

These and other objects, along with advantages and features of the present invention herein disclosed, will become apparent through reference to the following description, the accompanying drawings, and the claims. Furthermore, it is to be understood that the features of the various embodiments described herein are not mutually exclusive and can exist in various combinations and permutations.

BRIEF DESCRIPTION OF THE DRAWINGS

In the drawings, like reference characters generally refer to the same parts throughout the different views. Also, the drawings are not necessarily to scale, emphasis instead generally being placed upon illustrating the principles of the invention. In the following description, various embodiments of the present invention are described with reference to the following drawings, in which.

DESCRIPTION

Figure 1:
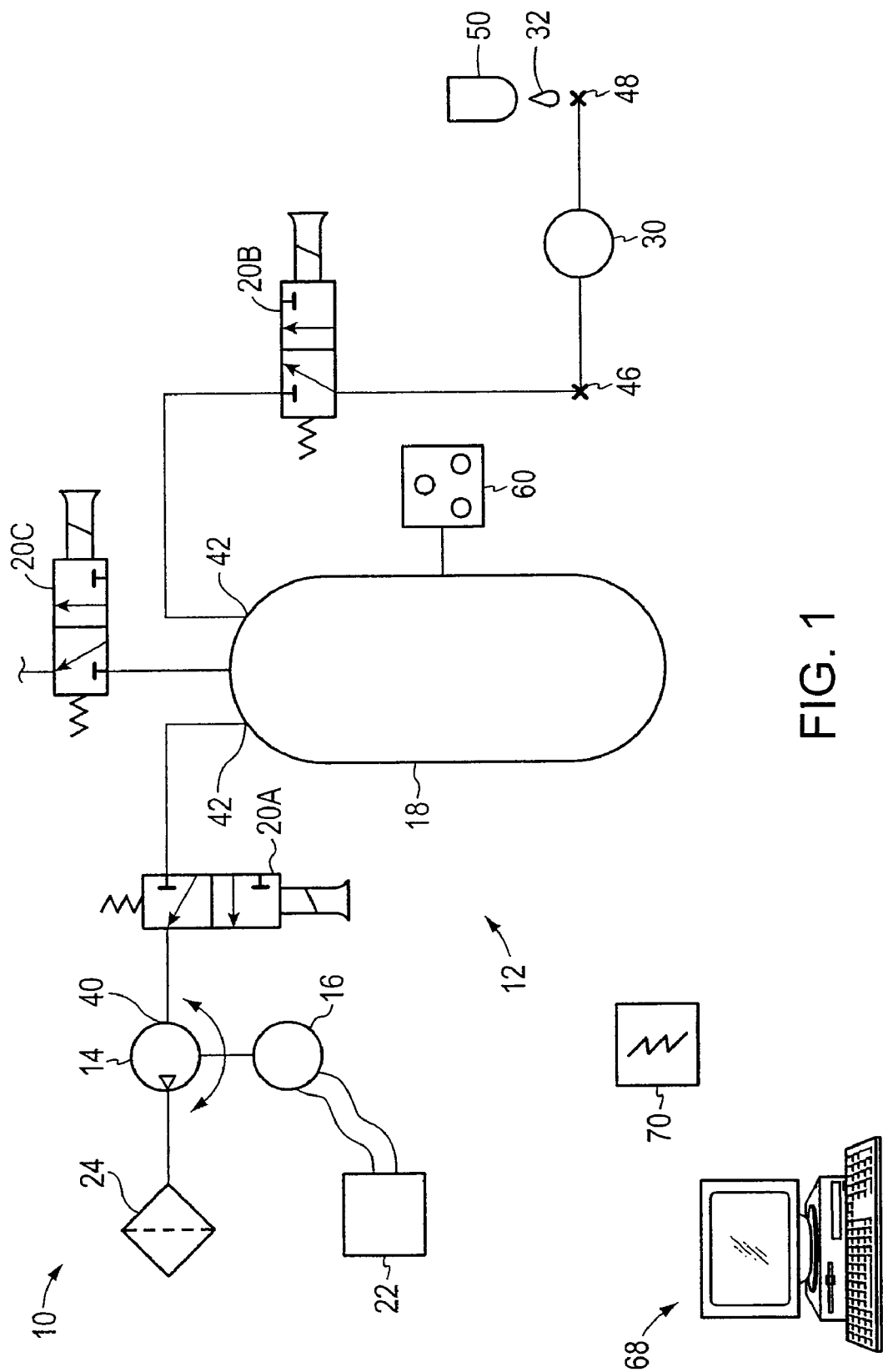
FIG. 1 is a schematic representation of one embodiment of an apparatus for handling microfluidic volumes in accordance with the invention.

Embodiments of the present invention are described below. It is, however, expressly noted that the present invention is not limited to these embodiments, but rather the intention is that modifications that are apparent to the person skilled in the art are also included. For example, many of the following embodiments are described with reference to pulling microfluidic volumes through a flow cell, however, the present invention can also be applied to pulling fluids through other types of analytical equipment, such as, for example, flow cytometers and chemical analyzers. Further, the apparatus can be used as part of a system for detecting single molecules by, for example, optical detection of single nucleotides.

In one embodiment, the apparatus 10 includes a vacuum source 12, an isolation valve 20, and a flow cell 30. In the embodiment depicted in FIG. 1, the vacuum source 12 is passive and includes a vacuum pump 14, a drive motor 16, and a reservoir 18. Alternatively, the vacuum source 12 could be non-passive, where the vacuum pump 14 is directly connected to the flow cell (see, for example, FIG. 3). In one embodiment, the vacuum pump 14 is a compact rotary vane type pump; however, the pump size and type will be selected to suit the particular application. For example, the pump could be a piston, gear, or diaphragm type pump. Further, the pump size will depend on the operating parameters of the apparatus 10, for example, the larger the pump capacity, the quicker the pump 14 will evacuate the reservoir 18. The drive motor 16 in one embodiment is a 12 volt DC electric motor; however, the motor size and type will be selected to suit the particular application. For example, larger flows may require a larger pump, which in turn may require a larger motor. Further, the pump 14 can be uni- or bi-directional and can be coupled to the motor 14 directly or via a flexible coupling or other means known to one of skill in the art. In a particular embodiment, the pump 14 and motor 16 are supplied as an assembly, such as model no. 50200 available from Thomas Pumps and Compressors of Shebogan, Wis.

The reservoir 18 in one embodiment is a four liter bottle, such as Nalgene® model no. 2125-4000 available from Nalge Nunc International of Rochester, N.Y. The reservoir size will be selected to suit a particular application and, as will be discussed in greater detail below, is typically substantially larger than the microfluidic volume to be pulled by the vacuum source 12. In addition, the reservoir material can be a metal, a polymer, glass, or combinations thereof. In particular, the reservoir material should be compatible with the microfluidic volume 32. Also, the reservoir 18 should be capable of withstanding the pressures to which the reservoir 18 is exposed. For example, the reservoir 18 should be able hold a vacuum with minimal leakage and without collapsing.

The apparatus 10 shown in FIG. 1 includes three valves, 20A, 20B, 20C (collectively 20). The valves 20 shown are two position, three connection type solenoid valves, such as model no. LHDA1233115H available from the Lee Co. of Westbrook, Conn. The solenoids, which actuate the valves, are energized by 12 volt DC; however, other voltages can be used and the valves can be actuated hydraulically, pneumatically, or manually. Additionally, the valve type and configuration can be selected to suit a particular application. For example, the valves can be two position, two connection or two position, four connection.

The first valve 20A is located between the reservoir 18 and the pump 14. In the unactuated state, the valve 20A isolates the reservoir 18 from the pump 14. The pump inlet 40 is connected to the atmosphere, while the reservoir outlet 42 is closed. Alternatively, the pump inlet 40 could be closed. When the first valve 20A is actuated, for example by energizing the solenoid, the valve 20A changes position, thereby connecting the pump inlet 40 to the reservoir outlet 42 and allowing the pump 14 (when running) to pull a vacuum on the reservoir 18. In one embodiment, the vacuum pressure is between about 1" Hg and about 29" Hg, preferably between about 2" Hg and 15" Hg, and more preferably between about 5" Hg and about 6" Hg; however, the vacuum pressure can be varied to suit a particular application. Generally, the greater the vacuum pressure, the faster the microfluidic volume 32 will be pulled through the flow cell. In some cases, a fast flow is desirable to reduce the amount of residue left within the flow cell 30 from the microfluidic volume 32.

The second valve 20B is located between the reservoir 18 and the flow cell 30. In the unactuated state, the valve 20B isolates the reservoir 18 from the flow cell 30. The reservoir inlet 44 is closed, while the flow cell outlet 46 is connected to the atmosphere. Alternatively, the flow cell outlet 46 could also be closed. When the second valve 20B is actuated, the valve 20B changes position, thereby connecting the flow cell outlet 44 to the reservoir inlet 46, which results in the vacuum within the reservoir 18 pulling the volume of material 32 through the flow cell 30. The vacuum pressure within the reservoir 18 determines the speed at which the volume 32 is pulled through the flow cell 30.

Optionally, a third valve 20C, as shown in FIG. 1, is connected to the reservoir 18 and is used to vent the reservoir 18. The optional third valve 20C could be located at a different location on the apparatus 10 to perform a different function. Alternatively or additionally, multiple valves 20 can be used in conjunction with multiple flow cells 30. For example, the apparatus 10 can include ten flow cells 30, or other analytical equipment, each connected in series with a valve 20 and the reservoir 18 (see, for example, FIG. 2).

Figure 9:
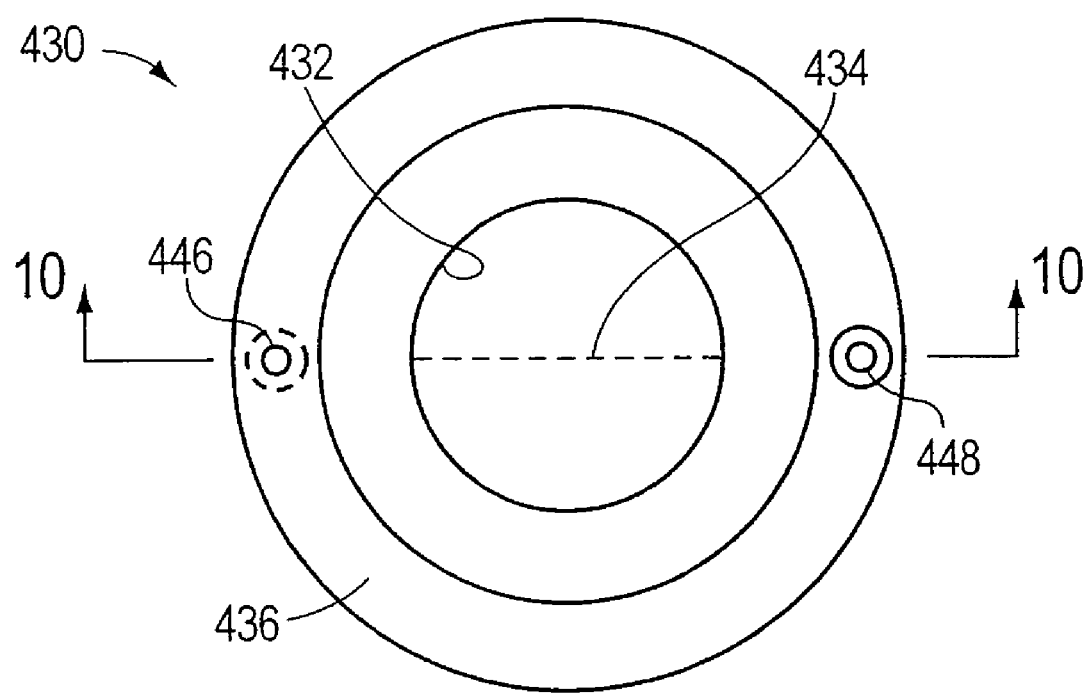
FIG. 9 is a plan view of a flow cell in accordance with one embodiment of the invention.
Figure 10:
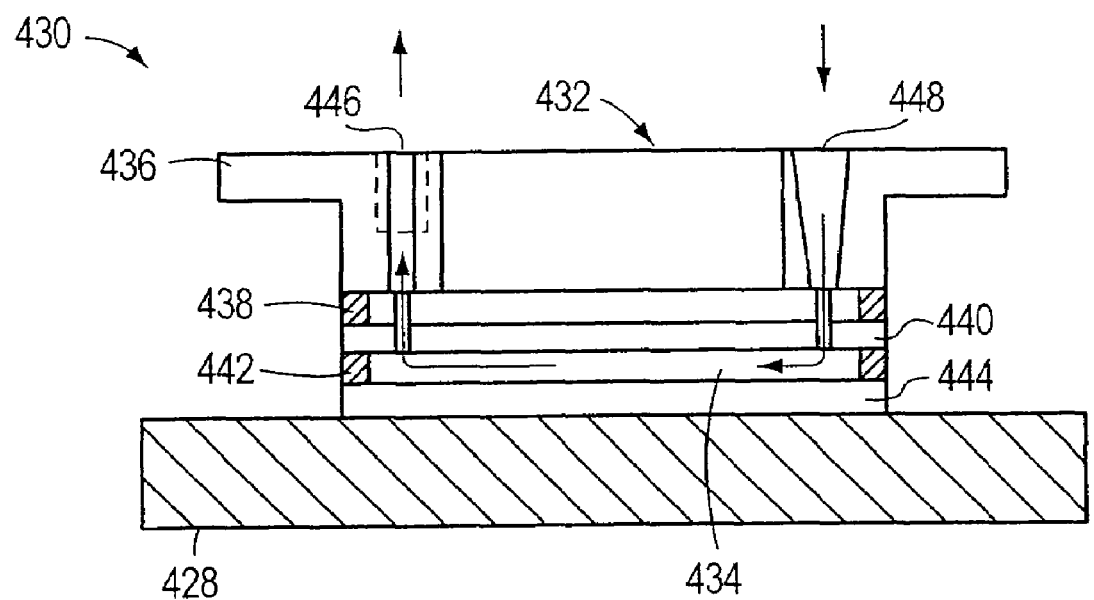
FIG. 10 is a cross-sectional view of the flow cell of FIG. 9 taken at line 10-10.
Figure 11:
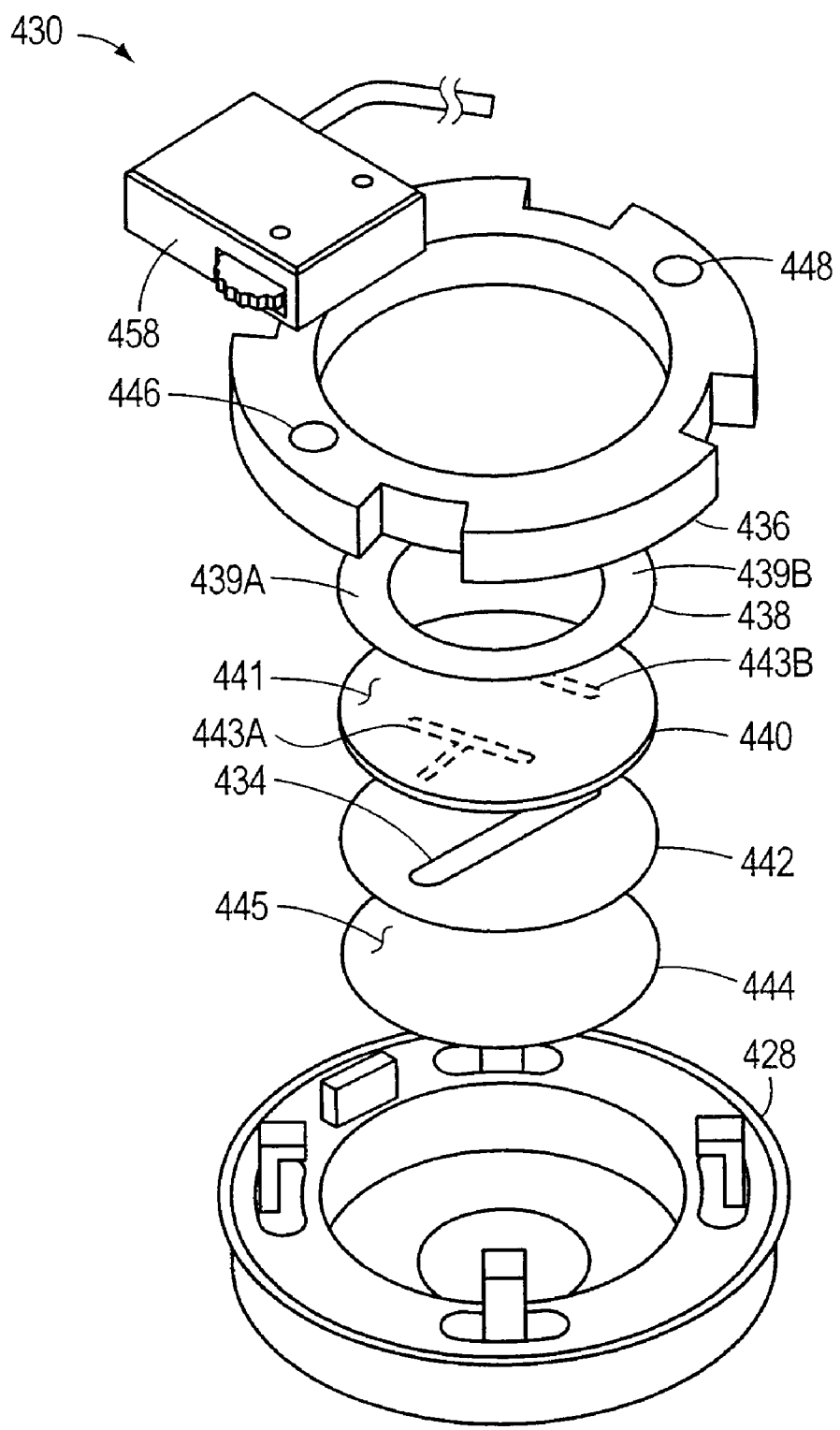
FIG. 11 is an exploded view of the flow cell of FIG. 9.

The flow cell 30 is coupled to the vacuum source 12, as described above. Multiple flow cells 30, or other analytical equipment, can be connected to the vacuum source 12 either in series or in parallel (see, for example, FIG. 2). In one embodiment, the flow cell 30 is a Focht Chamber System (model no. FCS2) available from Bioptechs of Butler, Pa. Alternatively, a customized flow cell system may be used. The flow cell 430 depicted in FIGS. 9-11 is a customized flow cell and will be described in greater detail with respect to FIGS. 9-11.

Further depicted in FIG. 1 is a pipette 50 for introducing the microfluidic volume 32 to the apparatus 10; however, other types of vessels can be used for introducing the volume 32 to the apparatus 10. For example, a cuvette or beaker could be used. The pipette 50 is positioned directly over the flow cell inlet 48. In one embodiment, the microfluidic volume 32 includes single molecules for use in sequencing deoxyribonucleic acid (DNA). In one embodiment, the pipette 50 can manually or automatically dispense individual microfluidic volumes in the range of about 2 microliters ($\mu$l) to about 2 milliliters (ml), preferably about 10 $\mu$l to about 100 $\mu$l, and more preferably about 20 $\mu$l. Further, the pipette 50 can be handled robotically to, for example, position the pipette 50 relative to the flow cell inlet 48, receive and mix materials within the pipette 50, and/or dispense precisely the microfluidic volume 32 based on time and/or volume.

The apparatus 10 further includes a pressure indicator 60, such as model no. DPG1000B-30INHGVAC available from Omega Engineering, Inc. of Stamford, Conn. The indicator 60 is used to measure the vacuum pressure within the reservoir 18; however, additional indicators can be used to measure the pressure at other locations in the apparatus 10, for example, the flow cell outlet 46. The indicator 60 can be a pressure gauge, a pressure transducer, and/or pressure switch, with or without a readout. For example, the pressure transducer could include a digital readout of the actual vacuum pressure within the reservoir 18 and/or the pressure switch can activate an alarm if the pressure within the reservoir 18 reaches a threshold value.

The apparatus 10 depicted in FIG. 1 also includes an optional controller 70. The controller 70 includes the electronic controls for operating, for example, the vacuum source 12 and valves 20 by, for example, a computer 68 and related software. The apparatus 10 can send and receive data directly or via the controller 70 to the computer 68. The computer 68 can be a conventional computer system including a processor, hard drive, RAM, a video monitor, and a keyboard, as may be found in a laboratory setting. The computer 68 can interact with the controller 70 to store and process data as necessary to operate the apparatus 10. Alternatively or additionally, the controller 70 can include an internal data processor. Alternatively, the apparatus 10 can be controlled manually. The controller 70 shown is a switch and sense type controller available from Measurement Computing Corporation of Middleboro, Mass. The exact controller configuration will be selected based on, for example, the number of inputs and outputs required and the type of equipment to be controlled. In one embodiment, the controller 70 can include the logic for cycling the pump 14 and motor 16 on and off and actuating the valves 20 based on predetermined time intervals and/or in response to signals from sensors. The controller can also supply the necessary power to the various components of the apparatus 10.

Figure 2:
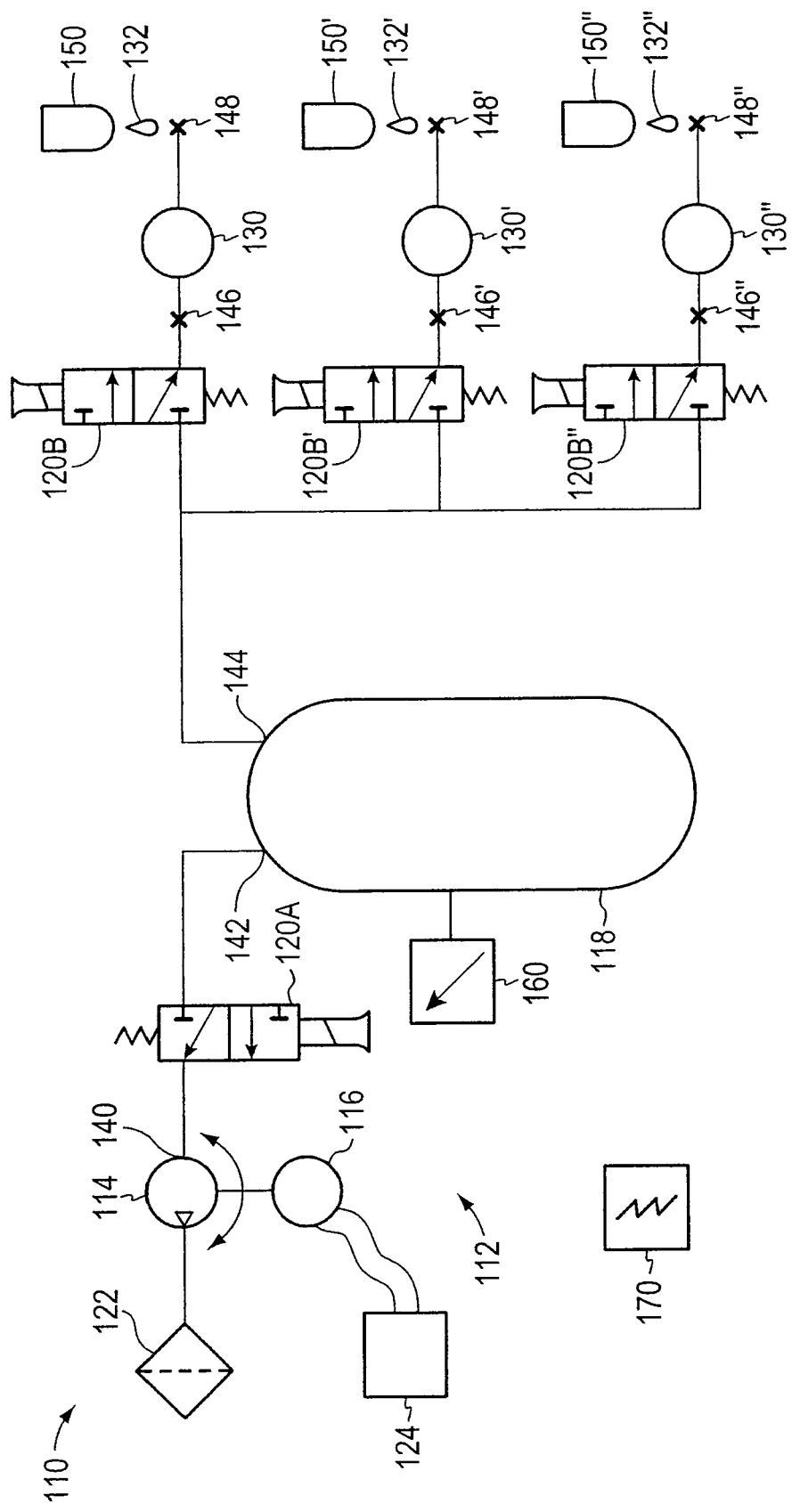
FIG. 2 is a schematic representation of an alternative embodiment of an apparatus for handling microfluidic volumes in accordance with the invention.

FIG. 2 depicts schematically an alternative embodiment of an apparatus 110 in accordance with the invention. The apparatus 110 is similar to the apparatus 10 described hereinabove with respect to FIG. 1; however, the apparatus 110 shown in FIG. 2 includes multiple flow cells 130, 130', 130" and corresponding second valves 120B, 120B', 120B" arranged in a parallel configuration. As described above, the apparatus 110 includes a passive vacuum system 112 including a pump 114, a motor 116, and a reservoir 118; a first valve 120A; a pressure indicator 160; and a controller 170.

The multiple flow cells 130, 130', 130" and the corresponding second valves 120B, 120B', 120B" are arranged in parallel to facilitate running multiple operations either simultaneously or sequentially. For example, the user can run three different operations without having to change set-ups between operations. The large $\Delta V$ between the reservoir 118 and the microfluidic volumes 32, 32', 32" facilitates multiple operations without any degradation in performance. Alternatively or additionally, the flow cells 130 could be arranged serially; however, serially arranged flow cells 130 would have to be operated simultaneously and may impact the adjacent flow cell(s) 130.

Figure 3:
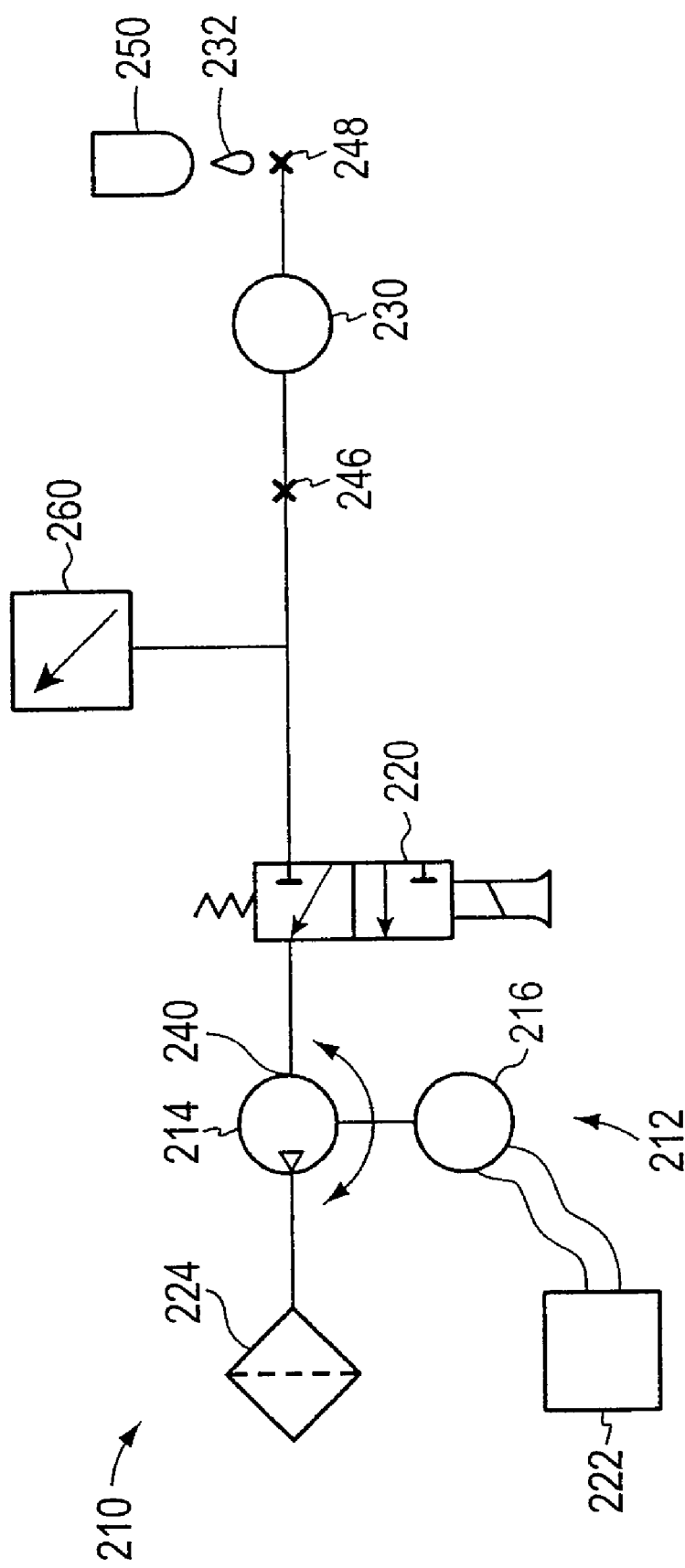
FIG. 3 is a schematic representation of another alternative embodiment of an apparatus for handling microfluidic volumes in accordance with the invention.

FIG. 3 depicts schematically another alternative embodiment of an apparatus 210 in accordance with the invention. The apparatus 210 is similar to the apparatus 10, 110 described hereinabove with respect to FIGS. 1 and 2; however, the apparatus 210 shown in FIG. 3 does not include a reservoir. The apparatus 210 includes a non-passive vacuum system 212 including a pump 214 and a motor 216, where the pump 214 is directly connected to the flow cell 230 via a single valve 220. The apparatus 210 further includes a pressure indicator 260 located between the pump inlet 240 and the flow cell outlet 246, and a controller 270.

Figure 4A:
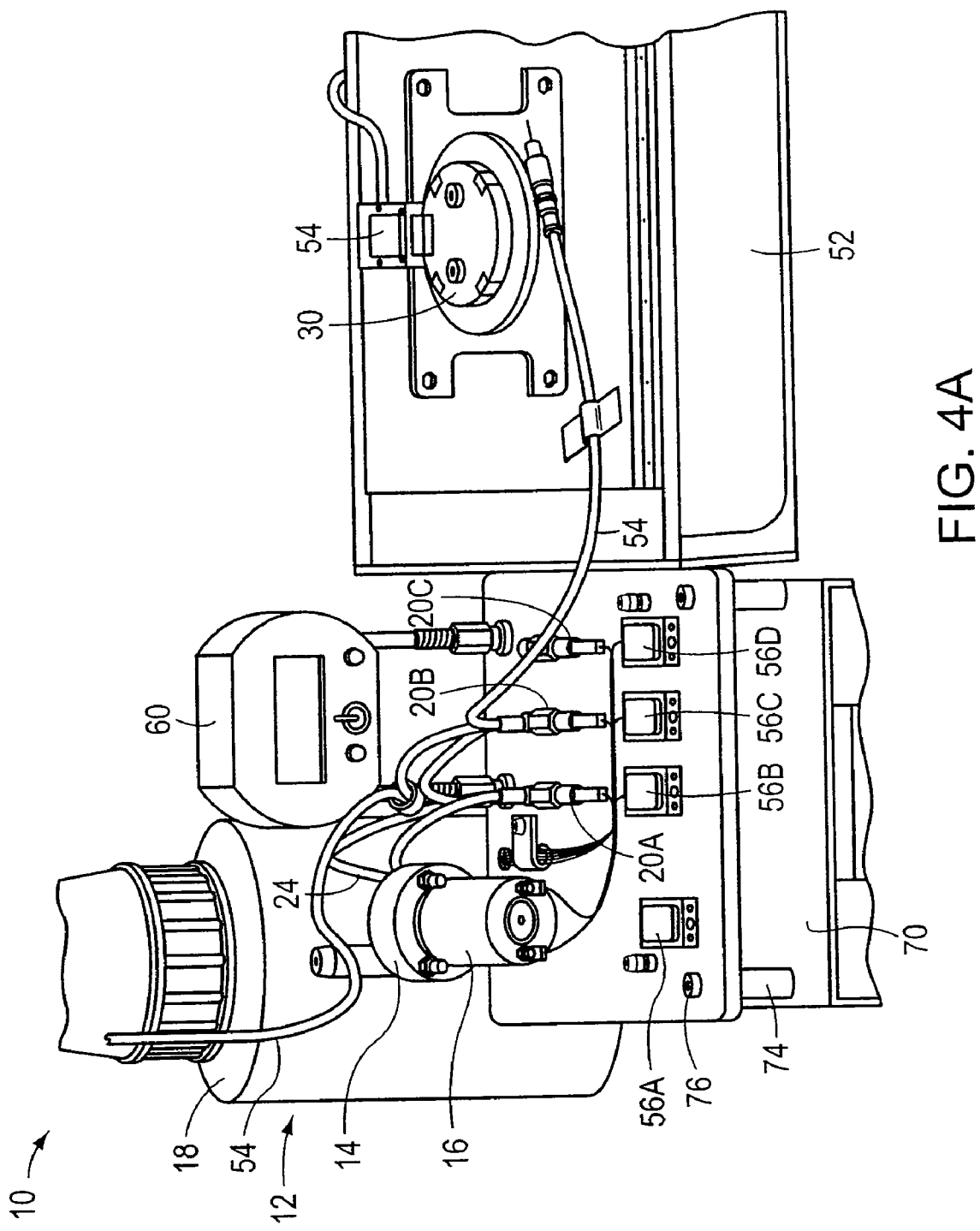
FIG. 4A is a pictorial representation of one possible configuration of the apparatus of FIG. 1.

FIG. 4A is a pictorial representation of one possible configuration of the apparatus 10 depicted schematically in FIG. 1. The vacuum system 12, valves 20, and indicator 60 are mounted on a breadboard 72; the reservoir 18 is free-standing adjacent to the breadboard 72; and the flow cell 30 is disposed on a microscope type stage 52 adjacent to the breadboard 72. The breadboard 72 is mounted on top of the controller 70 via stand-offs 74 and screws 76 located at the four corners of the breadboard 72. Also mounted on the breadboard 72 are push-buttons 56 for operating the valves 20, and the electrical and fluidic connections for the various components.

As shown in FIG. 4A, the apparatus 10 uses tubing 54 to connect the various components, for example, the pump 14 and reservoir 18. In one embodiment, the tubing 54 is capillary type tubing, which can be obtained from, for example, Polymicro Technologies, LLC of Phoenix, Ariz. Alternatively or additionally, conventional polymer tubing can be used, for example, ⅛" outside diameter nylon, such as Nylotube® available from New Age Industries, Inc. of Southampton, Pa. The size, type, and material of the tubing can be selected to suit a particular application. For example, metallic tubing may be undesirable for biological materials and the size of the tubing 54 should be selected based on the flow parameters of the microfluidic volumes. For example, the inside diameter of the tubing 54 should be sufficient to prevent turbulent flow of the microfluidic volume therethrough.

Moreover, the apparatus 10 can include various optical components, such as a microscope objective, a camera, and multiple light sources for optically analyzing the contents of the microfluidic volume 32 and/or the operation of the apparatus 10. Additionally, the flow cell 30 can be located on a microscope type stage 52 for optical viewing by the user. In one embodiment, the stage 52 can be moved in the X, Y, and/or Z directions to position the flow cell 30 relative to the optical components. In an alternative embodiment, the flow cell 30 is secured within a stationary fixture. Alternatively or additionally, the optical components can be movable in the X, Y, and/or Z directions. The apparatus 10 can also include additional sensors for monitoring various operations of the apparatus 10. For example, the apparatus 10 could include an optical sensor for monitoring the level of the microfluidic volume 32 within the flow cell inlet 48.

Figure 4B:
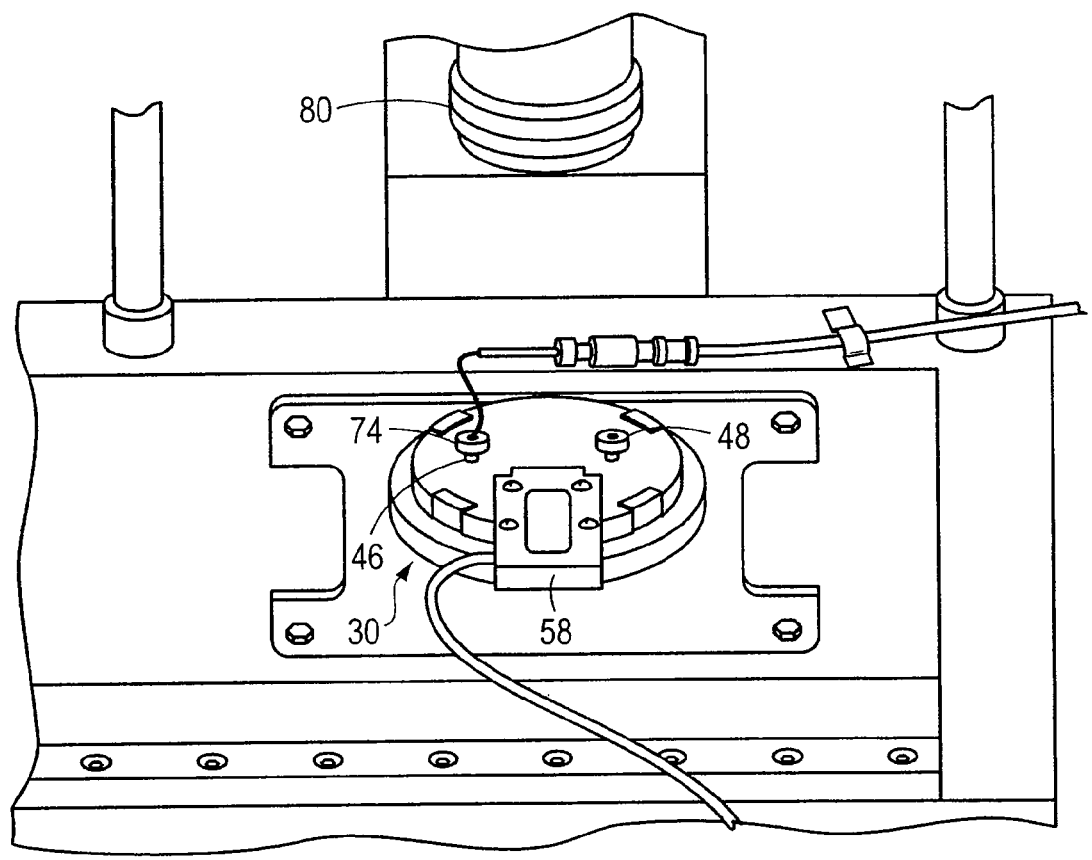
FIG. 4B is a pictorial representation of a portion of the apparatus of FIG. 4A.
Figure 5:
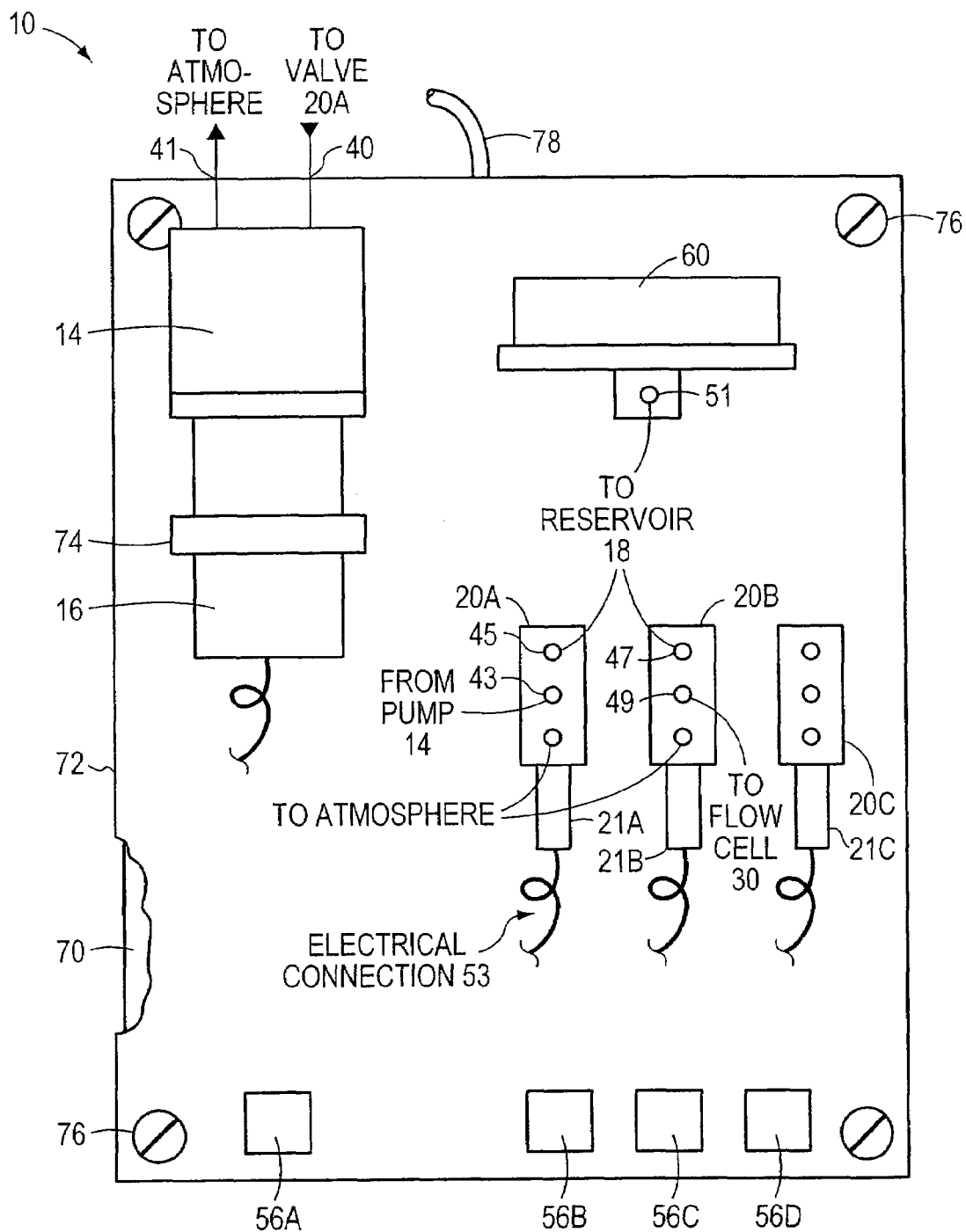
FIG. 5 is a plan view of a portion of the apparatus of FIG. 4A.
Figure 6:
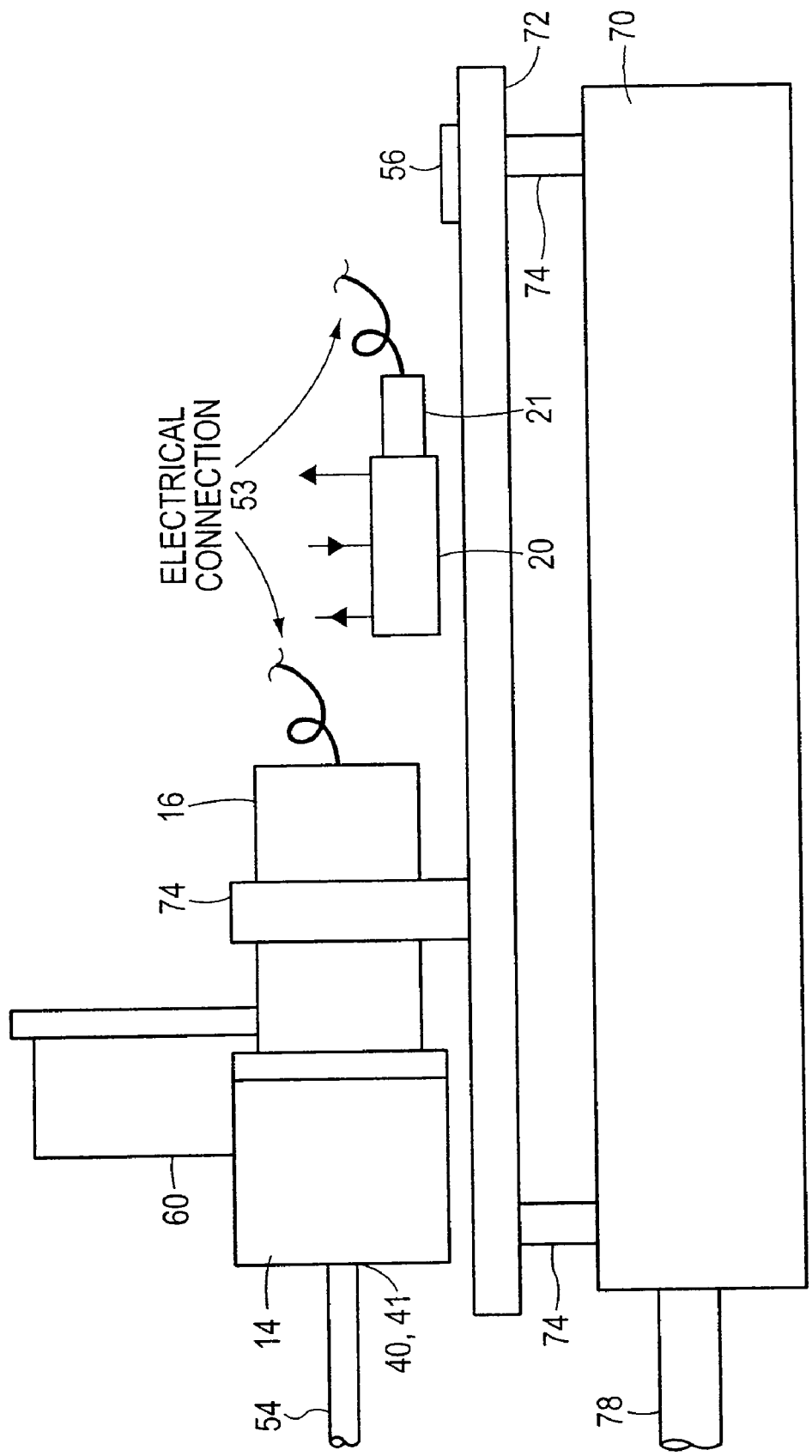
FIG. 6 is a side view of a portion of the apparatus of FIG. 4A.

FIG. 4B is a pictorial representation of a portion of the apparatus 10 shown in FIG. 4A. Specifically, FIG. 4B depicts an enlarged view of the flow cell 30 from the side opposite that shown in FIG. 4A. The flow cell inlet 48 is shown open and unobstructed. In operation, there would be a pipette located above the flow cell inlet 48. The pipette would contain and dispense the microfluidic volumes to be pulled through the flow cell 30. Shown above the flow cell inlet 48 is a camera 80 that can be used to display an image of the flow cell inlet 48 and the fluid flow therethrough to the user on, for example, an optional video monitor. Alternatively or additionally, the image can be used in conjunction with a sensor to send a signal to the controller 70 to, for example, close the second valve 20B. The flow cell outlet 46 is shown with a fitting and capillary tubing running therefrom. The fitting 74 is a conventional type of fitting that can be used to connect the tubing to the flow cell outlet 46, for example, a nut and ferrule type fitting. The tubing runs to the second valve 20B (see FIG. 4A). Shown adjacent to the flow cell 30 is a heater 58 that can be used to heat the various components, for example the flow cell 30, as needed to carry out a particular operation.

The apparatus 10 will be further described with reference to FIGS. 4A, 4B, 5, and 6. The pump 14 and motor 16 are mounted to the breadboard 72 by a bracket 74. The three valves 20 are also secured to the breadboard 72. The pump 14 has two connections; the inlet 40 and an outlet 41. The outlet 41 is open to the atmosphere, but could include an exhaust filter 24 (FIG. 1) or be plumbed to a remote location. The inlet 40 is plumbed to an outlet 43 on the first valve 20A via the tubing 54. The inlet 45 of the first valve 20A is than plumbed to the reservoir 18. The connections between the pump 14, valves 20, and reservoir 18 are push type fittings, where the tubing 54 is pushed over the fittings and secured by friction and/or barbs. Other types of fittings are also contemplated and considered within the scope of the invention.

An outlet 47 on the second valve 20B is plumbed to the reservoir 18. An inlet 49 on the second valve 20B is plumbed to the flow cell 30. The third valve 20C is optional in the depicted configuration and is, therefore, not shown plumbed. The pressure indicator 60 includes an inlet 51 that is plumbed to the reservoir 18 to continuously monitor the vacuum pressure therein.

Each of the valves 20 and the motor 16 include electrical connections 53. The electrical connections 53 are wired to the controller 70 for connection to the necessary power source(s) and control logic. The push buttons 56A, 56B, 56C, 56D (collectively 56) also include electrical connections that are wired to the valves 20, motor 16, and controller 70. The controller 70 includes an electrical connection 78 for connecting the controller 70 to the computer 68 (see FIG. 1). The controller 70 may include an additional connection for connecting to an external power source. In one embodiment, the electrical connection 78 is a USB connection. Alternatively or additionally, the controller 70 could include an IEEE 1394 connection, such as the FIREWIRE® brand sold by Apple Computer, Inc. The controller 70 can further include a power switch and indicators, either alone or as part of a user interface.

In the embodiment shown, the push buttons 56 are used to run the motor 16, which drives the pump 14, and to actuate the valves 20 by energizing the valve solenoids 21. Specifically, the first push button 56A, when pushed, energizes the motor 16, thereby causing the pump 14 to pull a vacuum. The second push button 56B, when pushed, energizes the first valve solenoid 21A, thereby connecting the pump 14 to the reservoir 18. When both push buttons 56A, 56B are pushed, the pump 14 evacuates the air out of the reservoir 18, thereby creating a vacuum within the reservoir 18. The third push button 56C, when pushed, energizes the second valve solenoid 21B, thereby connecting the reservoir 18 to the flow cell 30. The fourth push button, when pushed, energizes the third valve solenoid 21C, thereby actuating the third valve 20C. The apparatus 10 can include additional valves and push buttons as required by the specific configuration. In addition, other types of switches could be used to operate the various components, as opposed to the push buttons shown. For example, toggle type switches could be used.

Figure 7A:
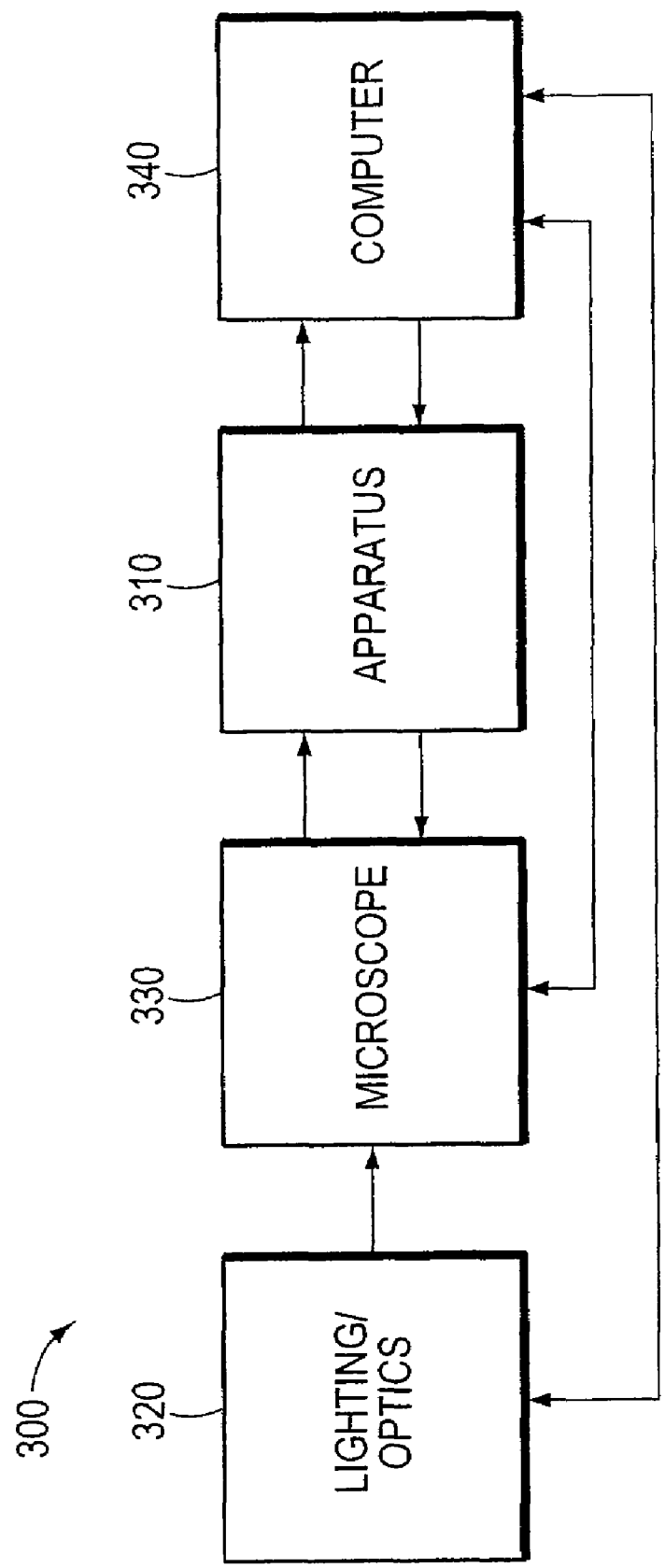
FIG. 7A is a block diagram of a system in accordance with one embodiment of the invention.
Figure 7B:
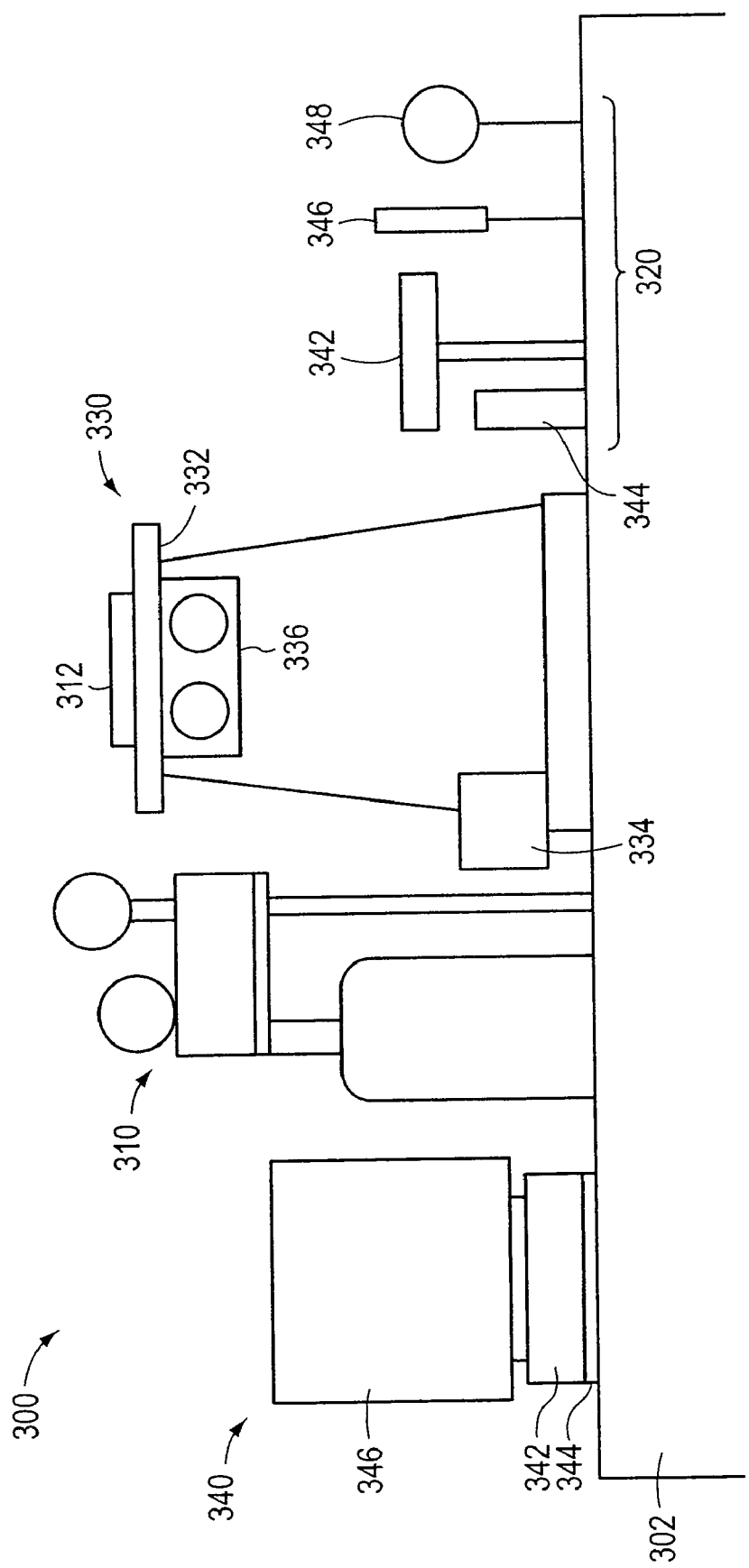
FIG. 7B is a pictorial representation of the system of FIG. 7A.

FIG. 7A depicts schematically an embodiment of a system 300 in accordance with the invention that includes an apparatus 310 and auxiliary components in accordance with the invention. FIG. 7B depicts one possible arrangement of the various components of the system. The auxiliary components include a lighting/optics module 320, a microscope module 330, and a computer module 340. Generally, in one embodiment, the lighting/optics module 320 includes multiple light sources and filters to provide light to the microscope for viewing and analysis. The light is reflected onto, for example, a flow cell 312 seated on the microscope module 330 (see FIG. 7B). The light can be multiple wavelengths, for example, one wavelength for viewing and another wavelength for analysis. A particular lighting/optics module 600 is described with respect to FIGS. 12A and 12B.

The microscope module 330 includes hardware for holding the flow cell 312 and moving the microscope stage and an imaging device, such as a camera. In some embodiments, the microscope module 330 is a part of the apparatus 310. The computer module 340 includes the memory and processors necessary for operating the various modules and a user interface for operating the system 300. The modules communicate with one another as shown by the arrows in FIG. 7A. For example, the computer module 340 may send a signal to the lighting/optics module 320 based on a user input to, for example, send a red light to the microscope module 330 to illuminate the flow cell. The computer module 340 can also send and receive signals from the microscope module 330 to change and monitor the position of the microscope stage or other operational parameters. Additionally, the computer module 340 can send and receive signals from the apparatus 310 to open and close valves.

As shown in FIG. 7B, the various components of the system 300 are mounted on a laboratory bench 302 in close proximity to one another; however, the arrangement of the various components can vary to suit a particular application and/or environment. The microscope module 330 includes a stage 332 for positioning the flow cell 312 or other item to be analyzed, a camera 334, and optics 336. Generally, a microscope, such as model no. TE2000 from Nikon Instruments, Inc. of Melville, N.Y., is suitable for use with the system 300; however, the type of microscope used can be selected based on the particular application and the nature of the sample to be analyzed.

The computer module 340 includes a processor 342, a video monitor 346, and a user interface 344, such as a keyboard and mouse for interacting with the system 300. In one embodiment, the camera 334 sends images to the computer module 340 for analysis and/or display on the video monitor 346. The lighting/optics module 320 of the system 300 includes an arrangement of light sources 342, 344 and filters 346 and mirrors 348 for conditioning the light emitted by the light sources 342, 344. The arrangement of the components will vary to suit a particular application and/or environment. The lighting/optics module 320 supplies conditioned light to the microscope module 330 for the viewing and analysis of the sample disposed therein.

Figure 8:
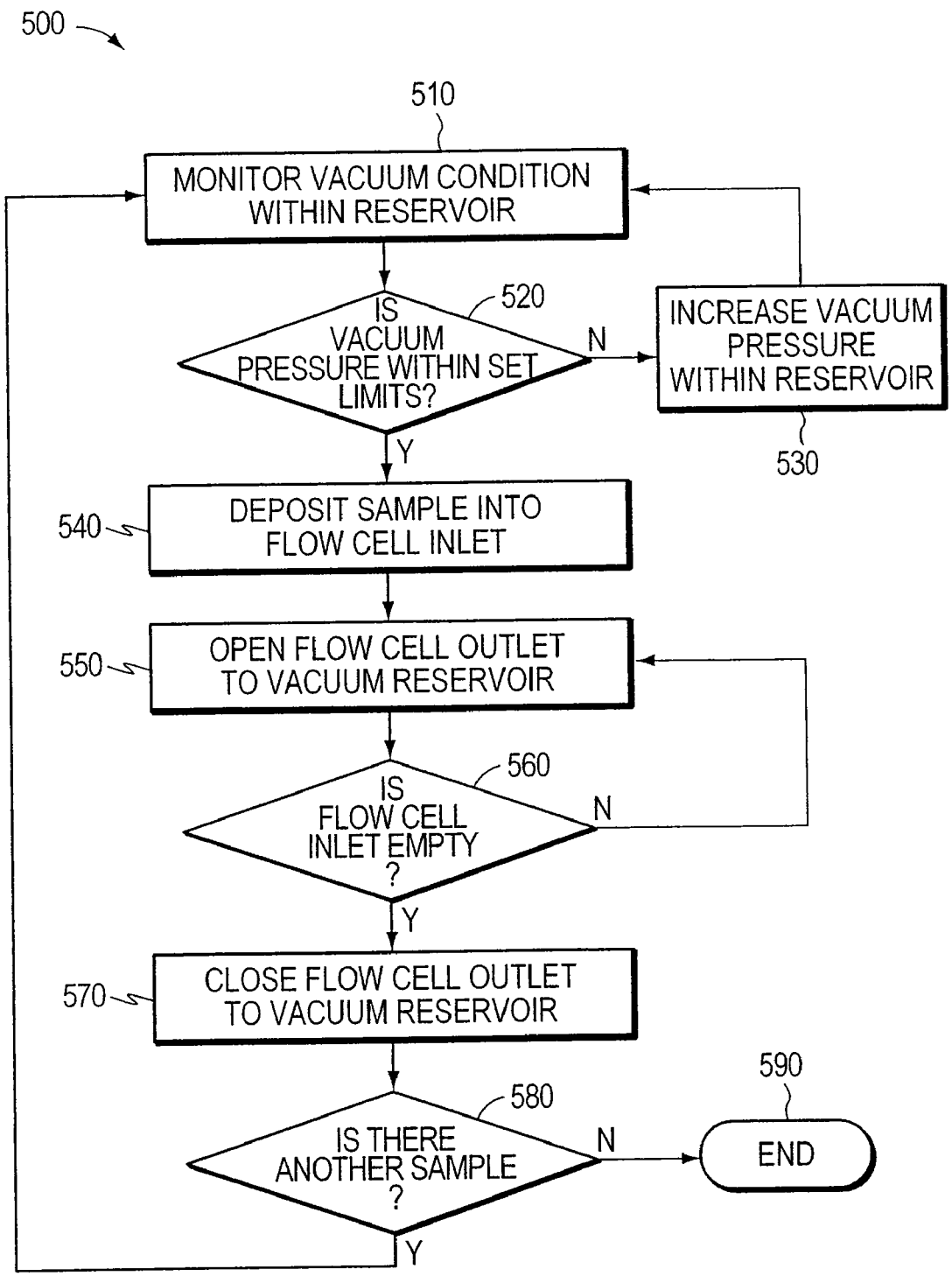
FIG. 8 is a flow chart depicting one mode of operation of a method of handling microfluidic volumes in accordance with the invention.

FIG. 8 represents the basic operation 500 of an apparatus in accordance with one embodiment of the invention. Generally, a user monitors the vacuum condition within the reservoir (step 510). If, for example, the vacuum level is not within set limits, the user can increase the vacuum pressure within the reservoir by operating the vacuum pump (Steps 520, 530). Once the vacuum pressure is within the set limits, the user can deposit a sample (e.g., a microfluidic volume) into the flow cell inlet (Step 540). Subsequently, the user will open the flow cell outlet to the reservoir, thereby pulling the sample through the flow cell (Step 550). Once the user or the controller determines that the flow cell inlet is empty (Step 560), the connection between the flow cell outlet and the reservoir is closed (Step 570). The user and or controller will maintain the connection between the flow cell outlet and the reservoir open until the flow cell inlet is empty, as it is desirable to pull essentially all of the sample through the flow cell to prevent contaminating subsequent operations. If there are additional samples to be pulled through the flow cell (Step 580), the basic operation is repeated until there are no more samples, at which time the operation is ended (Step 590). Alternatively or additionally, the sample to be analyzed is contained within the flow cell, where the sample is exposed to the material or volume of material pulled through the flow cell, thereby causing a reaction or otherwise effecting the sample within the flow cell.

More specifically, in operation, the user creates a vacuum in the reservoir 18 by, for example, operating the pump 14 and motor 16 and actuating the first valve 20A isolating the pump 14 from the reservoir 18. Once the desired vacuum is reached, for example about 6" Hg, the first valve 20A is deactuated and the pump 14 and motor 16 are stopped. Next, the pipette 50 deposits a microfluidic volume 32 within the flow cell inlet 48 and, subsequently, the second valve 20B is actuated, thereby connecting the vacuum reservoir 18 to the flow cell outlet 46 and pulling the microfluidic volume 32 through the flow cell 30 and into the reservoir 18, thus resulting in a transient exposure of the microfluidic volume and its contents to, for example, nucleotides that are held within the flow cell. Furthermore, the sample or volume can be driven through the flow cell by virtue of gravity, specifically the head of the volume held within the flow cell inlet or pipette. Once the microfluidic volume 32 leaves the flow cell inlet 48, the second valve 20B is closed, thereby removing the vacuum pressure from the flow cell 30. Generally, the second valve 20B should be open only long enough to pass the microfluidic volume 32 through the flow cell 30. If the valve 20B is open too long, air and bubbles can be pulled into the flow cell 30; if not open long enough, a portion of the volume 32 will remain in the flow cell 30, which could contaminate subsequent operations. Subsequently, the sample can be viewed and analyzed as desired.

In operation, it is desirable for the ratio of the reservoir volume 18 to the microfluidic volume 32 to be very large. For example, the ratio can be from about 1000:1 to about 2,000,000:1, preferably from about 50,000:1 to about 1,000,000:1, and more preferably about 200,000:1. In one embodiment, the reservoir 18 is about 4 liters (l) and the microfluidic volume is about 20 μl, thereby resulting in a ratio of about 200,000:1. The exact ratio will depend on, for example, the leakage rate of the reservoir, the size of the microfluidic volume, and the number of operations to be performed. A particularly large ratio results in the operation of the apparatus 10 being substantially unaffected by leakage and/or the number of microfluidic volumes 32 pulled through the flow cell 30, because the reservoir volume under vacuum is so great relative to the volumes being absorbed by the reservoir, the change in volume is negligible. For example:

$P_1V_1=P_2V_2$, where $P_1$=the vacuum pressure within the reservoir prior to adding the microfluidic volume ($\Delta V$);

$V_1$=the volume within the reservoir prior to adding $\Delta V$;

$P_2$=the vacuum pressure within the reservoir after adding $\Delta V$; and $V_2$=the volume within the reservoir after adding $\Delta V$.

Because $V_1$ is so large relative to $\Delta V$, $V_1$ is substantially equal to $V_2$. Therefore, $P_1$ is substantially equal to $P_2$.

The valves 20, pipette 50, and pump 14 can be operated manually or automatically. For example, the second valve 20B can be programmed to actuate (i.e., open) for "x" seconds after the pipette 50 deposits the volume 32 into the flow cell inlet 48 and deactuate (i.e., close) at the end of a set time period. In one embodiment, the time period can be adjusted to accommodate different volumes 32. In an alternative embodiment, an optical sensor can be used to actuate and/or deactuate the second valve 20B. For example, the second valve 20B can be actuated after the optical sensor senses that the appropriate volume 32 has been deposited into the flow cell inlet 48 and deactuated after the sensor senses that the flow cell inlet 48 is empty. In one embodiment, the sensor(s) will send a signal to the controller 70, which in turn outputs the appropriate response to the signal, e.g., deactuate the second valve 20B. Additionally, the pressure sensor 60 can be used to control the first valve 20A and the pump 14. For example, if the pressure sensor 60 senses that the vacuum in the reservoir 18 has degraded below a threshold value, the controller 70 can turn on the pump 14 and motor 16 and actuate the first valve 20A to increase the vacuum in the reservoir 18.

FIGS. 9, 10, and 11 depict the customized flow cell 430. The flow cell 430 is similar to the Focht Chamber System and includes a connection ring 436, an upper gasket 438, a slide 440, a lower gasket 442, a coverslip 444, and a locking base 428. Also shown is an optional heater 458. The connection ring 436 sits on top of the various components and when seated and locked in the base 428 seals the components in place. It is desirable to operate the flow cell 430 by pulling a volume through under vacuum, as opposed to a pushing the volume through by positive pressure. Positively pressurizing the flow cell 430 may result in the slide 440 and/or coverslip 444 being bowed outwardly, contamination being trapped between the gaskets 438, 442 and the slide 440 and/or coverslip 444, or otherwise compromising the integrity of the flow cell's structure. By using vacuum, the contact areas between the gaskets 438, 442 and the slide 440 and coverslip 444 are maintained, thereby eliminating the possibility of contamination collecting in those contact areas.

The connection ring 436 houses the flow cell inlet 448 and the flow cell outlet 446. In the embodiment shown, the inlet 448 and the outlet 446 are machined through the ring 436. The inlet 448 is a conical shaped recess and the outlet 446 is a threaded connection for accepting a fitting. The conical shaped inlet 448 is as large as possible to facilitate viewing the flow of any microfluidic volumes deposited therein. The connection ring 436 also defines a viewing area 432 where the slide 440 and coverslip 444 are visible. Further, the connection ring 436 should be made of a material that is dimensional stable, compatible with the microfluidic volumes passed therethrough, and to which any substances within the microfluidic volumes will not stick. Such materials include, for example, polyetheretherketone, sold by PLC Corporation under the trademark PEEK®; polyoxymethylene, sold by DuPont under the trademark Delrin®; polytetrafluoroethylene, sold by DuPont under the trademark Teflon®; and ethlene-chlorotrifluorethylene, sold by Allied Chemical Corporation under the trademark Halar®.

The upper gasket 438 provides the seal between the slide 440 and the connection ring 436. In the embodiment shown, the upper gasket 438 has a thin annular shape; however, the size and shape of the upper gasket 438 will vary to suit a particular application. The lower gasket 442 provides the seal between the slide 440 and the coverslip 444. In the embodiment shown, the lower gasket 442 covers a substantial portion of an upper surface of the coverslip 444. In particular, the lower gasket 442, along with a lower surface 441 of the slide 440, and an upper surface 445 of the coverslip 444, defines a flow channel 434 through which the microfluidic volumes travel. The size and shape of the flow channel 434 can be varied to suit a particular application. For example, the lower gasket 442 can be about 10 microns to about 3 millimeter (mm) thick, and can define an opening (flow channel 434) about 0.5 mm to about 5 mm wide, and the length of the opening can run substantially the entire width of the flow cell 430. In one embodiment, the lower gasket 442 is about 50 microns thick and the flow channel 434 is about 1 mm wide by about 25 mm long. Alternatively, the microfluidic flow channel 434 could be etched in the slide 440 and/or the coverslip 444.

In operation, the microfluidic volume is deposited into the flow cell inlet 448 on the connection ring 436 and is pulled through the flow cell 430 under vacuum. The volume travels through the flow cell 430 as shown by the arrows in FIG. 10. Specifically, the volume travels downwardly through the connection ring 436 and through openings 439B, 443B in the upper gasket 438 and the slide 440, and then into the flow channel 434 in the lower gasket 444. The volume then travels through the flow channel 434 defined by the coverslip 444, the slide 440, and the lower gasket 442. Once the volume reaches the opposing opening 443A in the slide 440, the volume is drawn upwardly through the openings 443A, 439A in the slide 440 and the upper gasket 438 and out the flow cell outlet 446 by the vacuum pressure within, for example, the reservoir. In various embodiments, the slide 440 and/or coverslip 444 can be treated to react with the microfluidic volume being pulled through the flow cell 430. For example, a plurality of DNA strings can be adhered to the coverslip in the area corresponding to the flow channel 434 in the lower gasket 442. Such an application is described in greater detail below.

One application for an apparatus in accordance with the invention includes performing single molecule sequencing. In this application, the flow cell includes individual strands of DNA or RNA (the template) bound to, for example, the coverslip 444 of the flow cell 430 (see FIGS. 9 and 10). The DNA or RNA can be bound to the coverslip by any known means for binding DNA or RNA to a surface using, for example, biotin-avidin interactions or other suitable attachment chemistries. A primer is added that hybridizes to a portion of the DNA or RNA bound in the flow cell.

The coverslip or other components of the flow cell that are exposed to the flow path of the microfluidic volume can be produced and sold with specific oligonucleotides bound thereto. Further, the coverslip material can include glass, quartz, silicon, or other materials present in commonly-available nucleic acid array chips. The material can incorporate an epoxide surface or another suitably reactive material to facilitate binding of the DNA or RNA to the surface.

In one embodiment, the DNA or RNA to be sequenced is immobilized on the slide or coverslip using a biotin/streptavidin linkage. Alternatively, immobilization can occur via the primer. For example, a biotinylated primer can be immobilized on the coverslip via streptavidin linked to biotin on the surface. Subsequent exposure of the immobilized primer to complementary DNA or RNA leads to sequence-specific hybridization with the DNA or RNA strand to be sequenced.

Next, a microfluidic volume comprising a polymerase and a solution of nucleotides is pulled through the flow cell and exposed to the bound templates. Complementary nucleotides will be incorporated in the primer. Detectable labels are used to improve detection. Detection, however, can occur by detecting the indicia of nucleotide incorporation, for example, heat produced by the reaction or pyrophosphate production resulting from incorporation. By monitoring nucleotide incorporation over time, the user can thus determine the sequence of the exposed nucleotide at that position on the slide or coverslip. Because the apparatus permits parallel monitoring of a very large number of individually-resolvable single molecules, each at a separate position on the coverslip, a correspondingly large amount of sequence information can be collected at one time. Thus, computer systems are useful to monitor the observed label during the process and for handling the resulting sequence data. Depending on the nature of the DNA or RNA molecules sequenced, the apparatus can be used, for example, to identify nucleic acid sequence variations associated with disease; to select or monitor a course of treatment; or to monitor gene expression in an individual or in a population of individuals.

In another embodiment, single nucleotide detection is accomplished by attaching template nucleic acids to a flow cell in the presence of a primer for template-dependent nucleic acid synthesis. Using a device according to the invention, a vacuum is created across the flow cell for introduction of reagents for template-dependent nucleic acid synthesis. For example, once template/primer pairs are bound to the surface of the flow cell, reagents comprising labeled or unlabeled nucleotides and a polymerase to catalyze nucleotide addition are added via the flow cell inlet. The vacuum is switched on and the reagents are exposed to the flow cell and then exit via the flow cell outlet to the reservoir. After a wash step, complementary nucleotides added to primer are detected. Preferably, reagent nucleotides are labeled with, for example, a fluorescent dye. Such dyes are observed using light microscopy. For example, cyanine dyes (cyanine-3 or cyanine-5) are useful for optical detection of incorporated nucleotides. Using optically-detectable labels, nucleic acid sequencing is conducted on a single molecule level. This means that individual template nucleic acids are positioned on the flow cell such that each is individually optically resolvable. The location of the templates is determined by, for example, the use of dye-labeled primers that hybridize to individual templates. Labeled nucleotides are flowed across the flow channel using the mechanisms described herein under conditions that allow complementary nucleotide addition to the primer. Once incorporated, the label is detected by excitation of the dye at the appropriate wavelength and by using an emission filter for detection of the emission spectrum. Emissions that occur at a location known to contain a template indicate incorporation of the labeled base at that position. By conducting these steps multiple times, a sequence is completed. Single molecule sequencing techniques are described in Braslavsky, et al., PNAS (USA), 100: 3960-3964 (2003) and copending U.S. patent application Ser. No. 09/707,737.

Figure 12A:
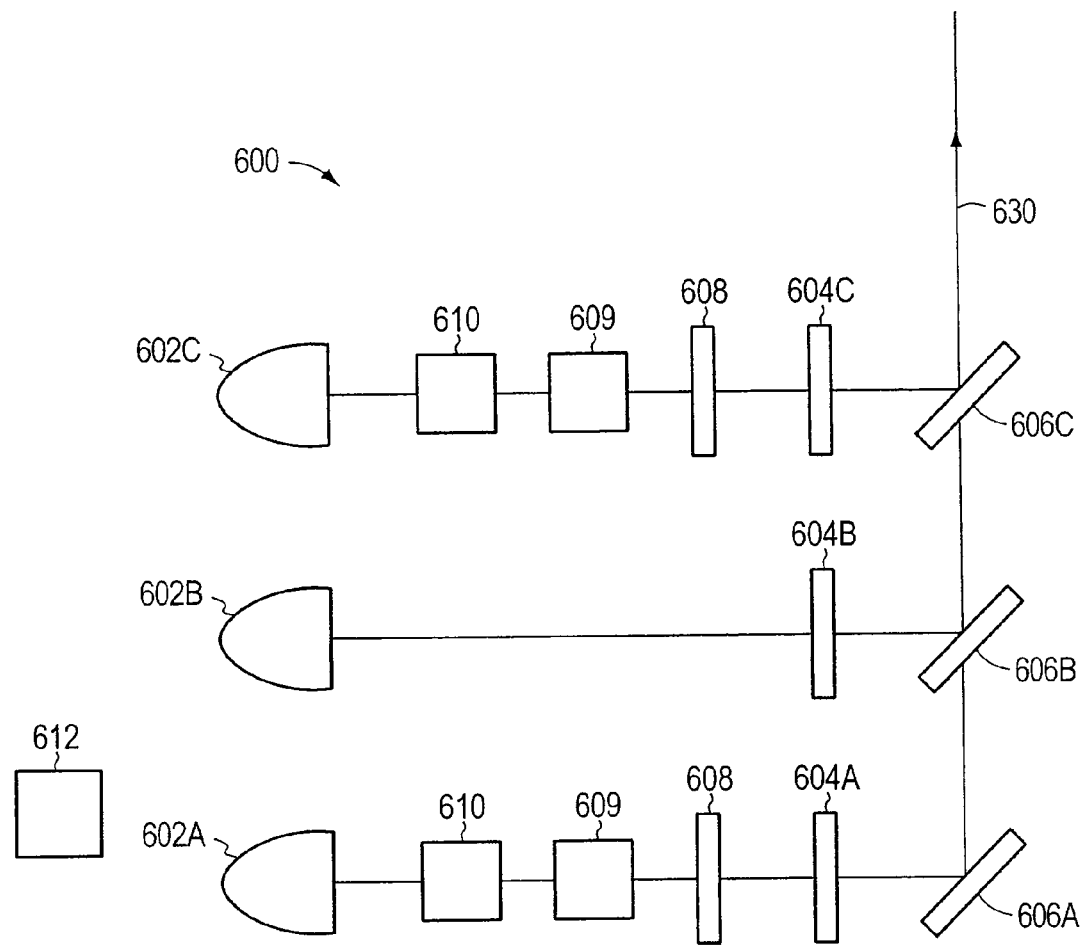
FIGS. 12A and 12B are schematic representations of a lighting system in accordance with one embodiment of the invention.
Figure 12B:
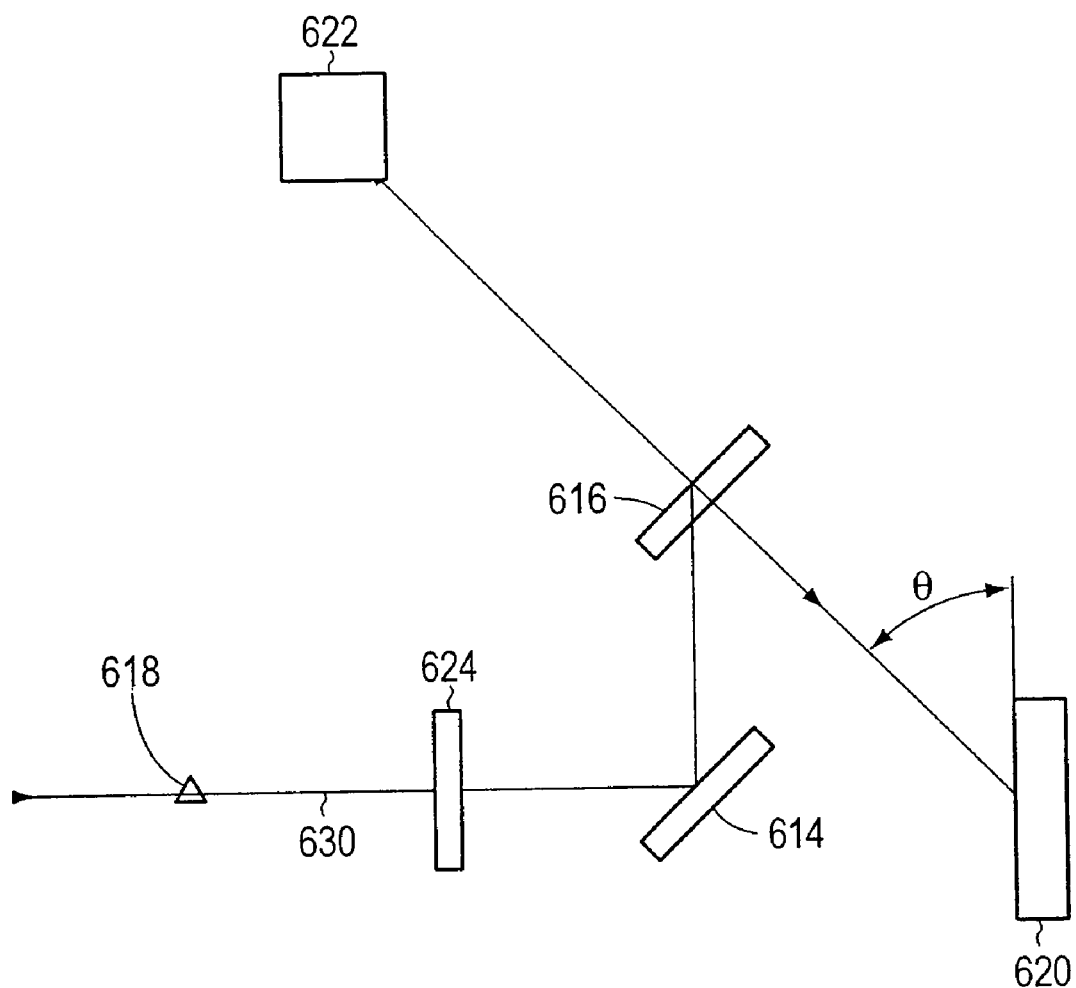

A system for analyzing a sample in accordance with one embodiment of the invention includes a lighting system 600. The lighting system 600, as shown in FIGS. 12A and 12B, may include a light source 602, a primary filter 604, a secondary filter 606, a shutter 608, a collimating lens 609, a focusing lens 610, and a power source 612. A first portion of the lighting system 600, shown in FIG. 12A, includes three light sources 602A, 602B, 602C (collectively 602). The lighting system 600, however, may include only two light sources or additional light sources as needed. The light source 602 can include lasers, light emitting diodes, or lamps. In one embodiment, the first light source 602A has a wavelength from about 390 nm to about 780 nm. In one embodiment, the first light source 602A is a red laser. The second light source 602B has a wavelength from about 936 nm to about 1340 nm. In one embodiment, the second light source 602B is an infrared laser. The third light source 602C has a wavelength from about 390 nm to about 780 nm. In one embodiment, the third light source 602C is a green laser.

The lighting system 600 shown in FIG. 12A also includes three primary filters 604A, 604B, 604C (collectively 604). The primary filters 604 can include notch filters. The notch filters 604 are selected to transmit the desired wavelength and to block unwanted wavelengths emitted by each light source 602. Additionally, the lighting system 600 shown in FIG. 12A includes three secondary filters 606A, 606B, 606C (collectively 606). The secondary filters 606 can include dichroic filters. In one embodiment, the dichoric filters are placed at a 45° angle relative to the light source 602. With a dichroic filter positioned at a 45° angle relative to the light source 602, a light source that would have been transmitted by the filter is still transmitted by the filter, but a light source that would have been blocked by the filter is reflected at a 90° angle. The lighting system 600 can also include shutter(s) 608 for blocking the light source(s) 602. Additionally, the focusing lens 610 can be used for narrowing the beam emitted from the light source 602, and the collimating lens 609 can be used for re-expanding and collimating the beam from the light source 602 to the desired diameter. In one embodiment, the three light sources 602A, 602B, 602C are collimated to substantially the same diameter. It is desirable for the beams of the light sources 602 to be of substantially the same diameter and strength when they contact the sample of interest so that the field of illumination of the sample 620 is of equal size regardless of which light source 602 is used. Also, the lighting system 600 can include a power source 612 for providing power to the light sources 602. The lighting system 600 can also include one or more mirrors for altering the optical path of the light sources as needed.

The lighting source 602 is directed to a desired point. As shown in FIG. 12B, the first light source 602A can define a first optical path 630 that intersects a sample of interest 620. The second light source 602B can be used to determine the position of the first optical path 630. Referring to FIG. 12A, the first light source 602A emits a beam of light of a desired wavelength in a desired optical path 630. The beam of light passes through the focusing lens 610 that narrows the beam and then through the collimating lens 609 that re-expands and collimates the beam to a desired diameter. The beam of the first light source 602A can be blocked by shutter 608 or allowed to pass through as desired. The beam of light passes through the notch filter 604A, where only the light of the desired wavelength is permitted to pass through. The beam of light from the first light source 602A then reflects off the first dichroic filter 606A at a 90° angle to the angle of incidence. The beam of light from the first light source 602A passes through the subsequent or downstream dichroic filters 606B, 606C in the desired optical path 630.

A second light source 602B emits a beam of light of a desired wavelength. The beam of light then passes through notch filter 604B, where only the light of the desired wavelength is allowed to pass through. The beam of light from the second light source 602B then reflects off the dichroic filter 606B at a 90° angle to the angle of incidence, such that the beam of the second light source 602B is at least substantially coaxial (i.e., propagates along the same axis) with the optical path 630 of the beam of the first light source 602A. The beams from the first light source 602A and the second light source 602B have substantially the same diameter. Both the beam from the first light source 602A and the beam from the second light source 606B pass through the third dichroic filter 606C.

A third light source 602C, which may be used in addition to or as an alternative to the first light source 602A, emits a beam of light of a desired wavelength. The beam of light passes through the focusing lens 610 that narrows the beam and then through the collimating lens 609 that re-expands and collimates the beam to the desired diameter. The beam can be blocked by the shutter 608 or allowed to pass through. The light then passes through the third notch filter 604C where only the light of the desired wavelength is allowed to pass through. The beam of light from the third light source 602C then reflects off the third dichroic filter 606C at a 90° angle to the angle of incidence, such that the beam of the third light source 602C is at least substantially coaxial with the first light source 602A and/or the second light source 602B. The beam of the third light source 602C has substantially the same diameter as the beams from the first light source 602A and second light source 602B.

Because the first light source 602A and the third light source 602C can be independently blocked, variations of which beams are directed to the desired position are possible. For example, the third light source 602C can be blocked so that only the first light source 602A and the second light source 602B are directed to the desired point. Alternatively, all three light sources 602A, 602B, 602C, can be directed to the desired point at the same time. In some embodiments, the lighting system can also include a neutral density filter 624 that is used to adjust the density of the light that is allowed to contact the sample 620. For example, if the sample 620 is saturated with light, the neutral density filter 624 can be adjusted to reduce the strength of the light directed to the sample 620. The neutral density filter 624 can be disposed along the optical path 630.

As shown in FIG. 12B, the optical path 630 of the coaxial beam of the light source 602 is directed to a mirror 614 (or alternatively a dichroic filter). The optical path is reflected at a 90° angle to the angle of incidence towards a filter 616. The beam from the first light source 602A and/or the third light source 602C reflects off filter 616 at a 90° angle to the angle of incidence towards the sample of interest 620. The beam of the second light source 602B is refracted by the filter 616 towards a position sensor 622 that senses the angle of reflection of the optical path 630 relative to the sample 620.

The information provided by the position sensor 622 could be used to adjust the angle θ at which the optical path 630 of the light source 602A intersects the sample 620. For example, the stage upon which the sample resides could be repositioned with respect to the optical path 630 and/or the orientation of the mirror 614 could be adjusted. Alternatively, the lighting system 600 could include a translator 618 that can be used to modify the angle of the optical path 630 of the light source 602A towards the mirror 614. The translator 618 can include a micrometer that is used to set the desired angle θ of the optical path 630.

The desired optical path 630 is one that results in total internal reflection of the beam of the light source 602A relative to the sample of interest 620. The angle θ is the critical angle, and its value depends on the refractive indices of the media ($\theta = \sin^{-1}$ (dense medium/less-dense medium). Thus the angle θ depends on the density of the glass (i.e., "dense medium"), the quality of the surface of the glass, and the density of the sample (i.e., "less-dense medium").

The position sensor 622 can be in communication with a computer, which can send a signal to automatically adjust the direction of the optical path 630 in response to a signal from the position sensor 622. Alternatively, the position sensor 622 could have a read out that informs the user of the angle of reflection θ of the optical path 630, which in turn could be manually adjusted. The angle θ of reflectance of the optical path 630 can be continuously monitored and adjusted as necessary to maintain the critical angle θ, as the system operates.

When the light source 602 hits the sample 620 at the desired angle θ, all of the light is reflected (i.e., there is total internal reflection). Some of the energy of the beam, however, still propagates a short distance into the less dense medium, generating an evanescent wave. A flourophore molecule attached to the sample of interest 620 absorbs photons of the evanescent wave and is excited. The excited fluorophores can be observed using, for example, an intensified CCD camera.

The lighting system as illustrated in FIGS. 12A and 12B, and as described above, is one possible arrangement of components of a lighting system in accordance with the invention. Other embodiments using different component arrangements, including different quantities and types of components such as filters and mirrors, are contemplated and considered within the scope of the invention. For example, multiple components can be used for conditioning the light source and adjusting the optical path or additional light sources could be used. Also, multiple sensors could be used to determine the angle of reflectance θ of the optical path 630.

Having described certain embodiments of the invention, it will be apparent to those of ordinary skill in the art that other embodiments incorporating the concepts disclosed herein may be used without departing from the spirit and scope of the invention. The described embodiments are to be considered in all respects as only illustrative and not restrictive.

What is claimed is:

1. A system for analyzing a sample, comprising:
 a flow cell;
 a lighting system for illuminating the sample in the flow cell; and
 an optical instrument for viewing the sample in the flow cell,
 wherein the lighting system comprises:
 one or more analytical light sources, each light source defining an optical path that intersects the sample; and
 a focusing light source operating with any one of the analytical light sources to focus said optical instrument on the sample.

2. The system of claim 1, wherein the optical system comprises two or more analytical light sources.

3. The system of claim 1, further comprising a stage for receiving the flow cell, wherein the stage is movable in at least one direction.

4. The system of claim 1, wherein at least one of the analytical light sources and the focusing light source operate simultaneously.

5. The system of claim 1, wherein light from the focusing light source defines a second optical path at least partially coaxial with one of the analytical optical paths.

6. The system of claim 1, wherein at least one of the analytical light sources emits light with a wavelength from about 390 nm to about 780 nm.

7. The system of claim 2, wherein each of the analytical light sources emit light of a different wavelength.

8. The system of claim 1, wherein the focusing light source emits infrared light.

9. The system of claim 1, wherein the flow cell comprises a surface for receiving a nucleotide.

10. The system of claim 9, wherein the surface of the flow cell comprises a primer for binding the nucleotide thereto.

11. The system of claim 10, wherein the primers are optically resolvable as single molecules.

12. The system of claim 11, wherein the binding of the nucleotide is polymerase mediated.

13. The system of claim 1, wherein the illumination and viewing employs total internal reflection fluorescence (TIRF).

* * * * *